US012064585B2

(12) United States Patent
Stumpe et al.

(10) Patent No.: US 12,064,585 B2
(45) Date of Patent: Aug. 20, 2024

(54) CONNECTOR

(71) Applicant: UNOMEDICAL A/S, Lejre (DK)

(72) Inventors: Tobias Stumpe, Lejre (DK); Pernelle Kruse Schøndorff, Lejre (DK); Jesper Erichsen, Lejre (DK)

(73) Assignee: UNOMEDICAL A/S, Lejre (DK)

( * ) Notice: Subject to any disclaimer, the term of this patent is extended or adjusted under 35 U.S.C. 154(b) by 694 days.

(21) Appl. No.: 17/039,091

(22) Filed: Sep. 30, 2020

(65) Prior Publication Data
US 2021/0093849 A1 Apr. 1, 2021

Related U.S. Application Data

(63) Continuation of application No. PCT/EP2020/077310, filed on Sep. 30, 2020.

(30) Foreign Application Priority Data

Oct. 1, 2019 (GB) ...................................... 1914132

(51) Int. Cl.
*A61M 39/10* (2006.01)
*A61M 5/14* (2006.01)

(52) U.S. Cl.
CPC ........ *A61M 39/105* (2013.01); *A61M 5/1407* (2013.01); *A61M 2230/201* (2013.01)

(58) Field of Classification Search
CPC .............. A61M 39/105; A61M 5/1407; A61M 2230/201; A61M 5/14248; A61M 2005/1585; A61M 5/1413; A61M 5/158
See application file for complete search history.

(56) References Cited

U.S. PATENT DOCUMENTS

| 11,040,135 | B2 | 6/2021 | Clemente et al. |
| 11,065,381 | B2 | 7/2021 | Naftalovitz et al. |
| 11,135,356 | B2 | 10/2021 | Hanson et al. |
| 11,135,362 | B2 | 10/2021 | DiPerna et al. |
| 11,136,971 | B2 | 10/2021 | Kamen et al. |

(Continued)

FOREIGN PATENT DOCUMENTS

| AU | 2019216642 A1 | 9/2019 |
| EP | 3556411 B1 | 6/2021 |

(Continued)

OTHER PUBLICATIONS

International Search Report; European Patent Office; International Application No. PCT/EP2020/077310; Dec. 4, 2020; 5 pages.

(Continued)

*Primary Examiner* — Theodore J Stigell
(74) *Attorney, Agent, or Firm* — TAFT STETTINIUS & HOLLISTER LLP; Ryan O. White; Derek B. Lavender

(57) ABSTRACT

The present disclosure relates to a connector for an infusion set. The connector comprises a body and at least one arm connected to the body which is configured to couple with a base of an infusion set; wherein the body has a first portion and a second portion which are configured to be removably and replaceably coupled together; and wherein each portion has a fluid delivery conduit, the conduits being configured to allow fluidic communication of the connector with at least two independent fluid sources. Also disclosed is an infusion set.

18 Claims, 14 Drawing Sheets

(56) References Cited

U.S. PATENT DOCUMENTS

| | | | |
|---|---|---|---|
| 11,141,530 B2 | 10/2021 | Moberg et al. | |
| 11,167,082 B2 | 11/2021 | Laurence et al. | |
| 11,173,244 B2 | 11/2021 | Agard et al. | |
| 11,266,777 B2 | 3/2022 | Gibson et al. | |
| 11,293,425 B2 | 4/2022 | Kamen et al. | |
| 11,311,670 B2 | 4/2022 | Barmaimon et al. | |
| 11,364,337 B2 | 6/2022 | Cabiri et al. | |
| 11,391,273 B2 | 7/2022 | Kamen et al. | |
| 11,413,391 B2 | 8/2022 | Gray | |
| 11,464,900 B2 | 10/2022 | Mccullough et al. | |
| 11,497,846 B2 | 11/2022 | Kamen et al. | |
| 11,517,663 B2 | 12/2022 | McCullough et al. | |
| 11,534,543 B2 | 12/2022 | Kamen et al. | |
| 11,690,952 B2 | 7/2023 | Kamen et al. | |
| 11,712,513 B2 | 8/2023 | Gray et al. | |
| 11,738,138 B2 | 8/2023 | DeStefano et al. | |
| 11,738,139 B2 | 8/2023 | Gray | |
| 11,744,940 B2 | 9/2023 | Weiser et al. | |
| 2006/0264908 A1 | 11/2006 | Ishii et al. | |
| 2008/0262425 A1 | 10/2008 | Mogensen | |
| 2009/0062767 A1* | 3/2009 | Van Antwerp | A61B 5/6849 600/316 |
| 2011/0230838 A1 | 9/2011 | Adams et al. | |
| 2011/0313357 A1* | 12/2011 | Skutnik | A61M 25/007 264/254 |
| 2018/0117296 A1* | 5/2018 | Damiano | A61M 5/142 |
| 2021/0170153 A1 | 6/2021 | Ross et al. | |
| 2021/0180583 A1 | 6/2021 | Gray | |
| 2021/0180584 A1 | 6/2021 | Kamen et al. | |
| 2021/0190063 A1 | 6/2021 | Gray | |
| 2021/0196892 A1 | 7/2021 | Dasbach et al. | |
| 2021/0293232 A1 | 9/2021 | Kamen et al. | |
| 2021/0321914 A1 | 10/2021 | Brister et al. | |
| 2021/0369957 A1 | 12/2021 | Wieser et al. | |
| 2021/0386930 A1 | 12/2021 | Anigan et al. | |
| 2021/0396221 A1 | 12/2021 | Kamen et al. | |
| 2021/0402083 A1 | 12/2021 | Gibson et al. | |
| 2022/0001106 A1 | 1/2022 | DiPerna et al. | |
| 2022/0047808 A1 | 2/2022 | Gibson et al. | |
| 2022/0054741 A1 | 2/2022 | Laurence et al. | |
| 2022/0118177 A1 | 4/2022 | Burgess et al. | |
| 2022/0184303 A1 | 6/2022 | DiPerna et al. | |
| 2022/0218900 A1 | 7/2022 | Gibson et al. | |
| 2022/0275796 A9 | 9/2022 | Kamen et al. | |
| 2022/0347388 A1 | 11/2022 | Norton et al. | |
| 2022/0379019 A1 | 12/2022 | Lanigan et al. | |
| 2023/0226273 A1 | 7/2023 | Kamen et al. | |
| 2023/0226274 A1 | 7/2023 | Kamen et al. | |
| 2023/0270934 A1 | 8/2023 | DeStefano et al. | |

FOREIGN PATENT DOCUMENTS

| | | |
|---|---|---|
| EP | 3832661 A1 | 6/2021 |
| EP | 3834864 A1 | 6/2021 |
| EP | 3848069 A1 | 7/2021 |
| EP | 3233163 B1 | 10/2021 |
| EP | 3711793 B1 | 12/2021 |
| EP | 3760253 B1 | 4/2022 |
| EP | 3756704 B1 | 5/2022 |
| EP | 2262550 B1 | 8/2022 |
| EP | 3027246 B1 | 8/2022 |
| EP | 3256189 B1 | 10/2022 |
| EP | 3035978 B1 | 9/2023 |
| EP | 3769802 B1 | 9/2023 |
| WO | 2010080715 A1 | 7/2010 |
| WO | 2015061690 A1 | 4/2015 |
| WO | 2017007968 A1 | 1/2017 |

OTHER PUBLICATIONS

Written Opinion of the International Searching Authority; European Patent Office; International Application No. PCT/EP2020/077310; Dec. 4, 2020; 7 pages.

* cited by examiner

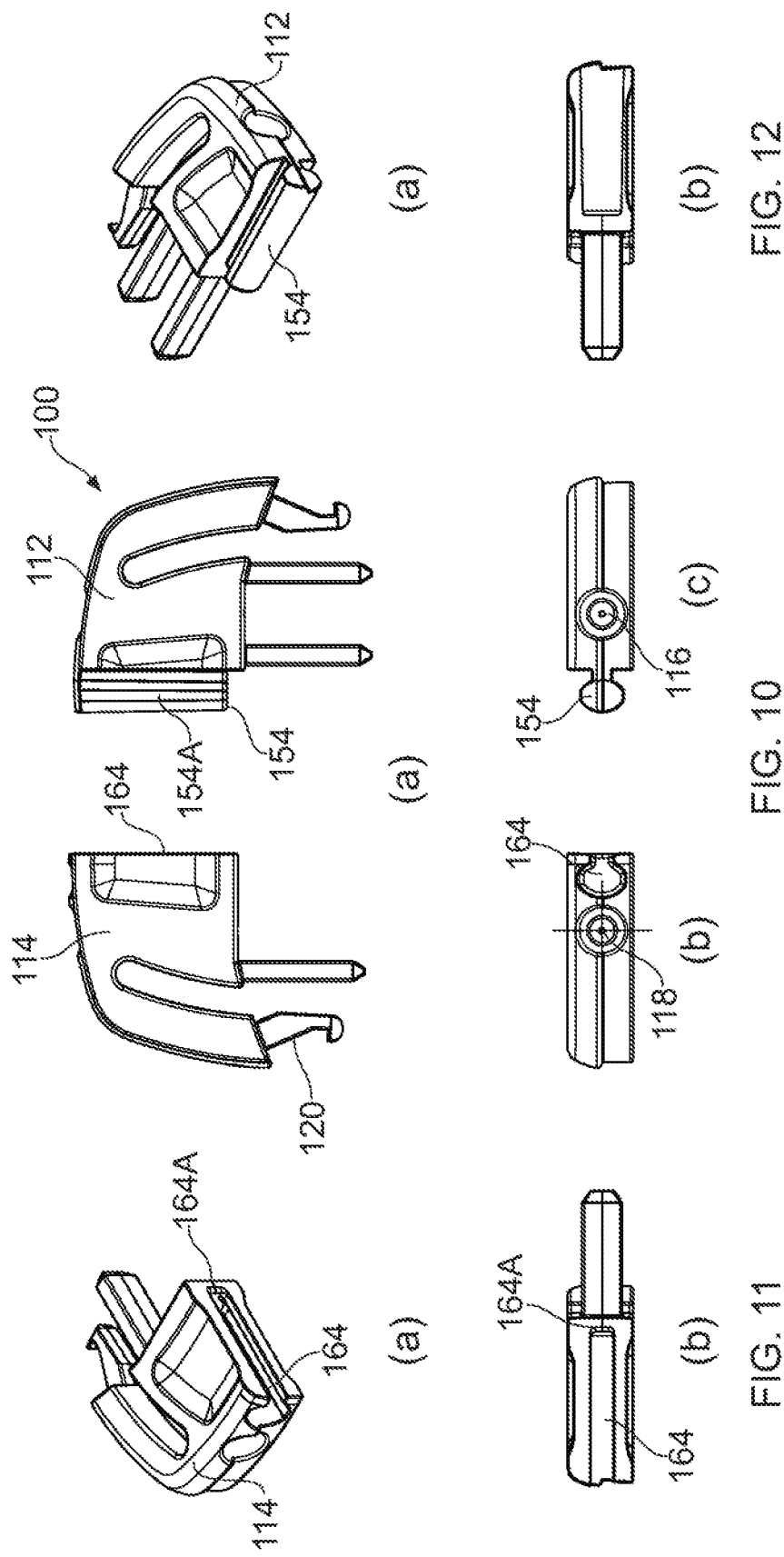

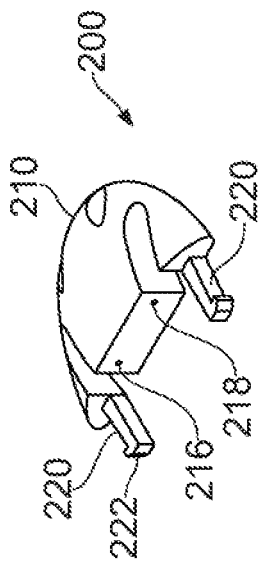
FIG. 14
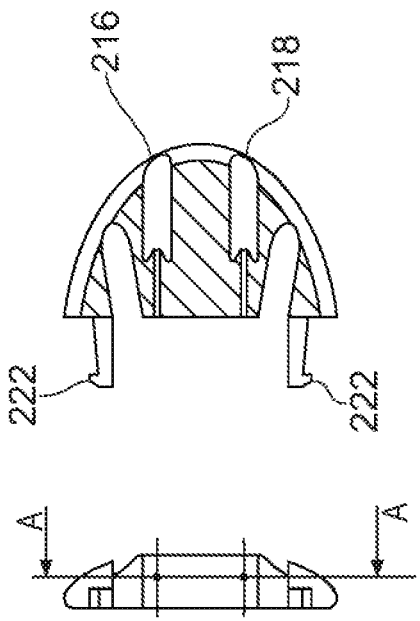
FIG. 17
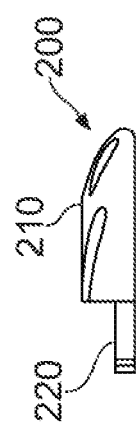
FIG. 13
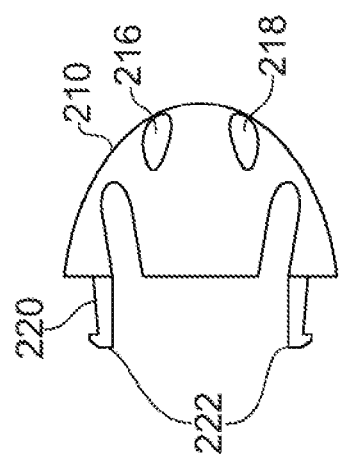
FIG. 16
FIG. 15

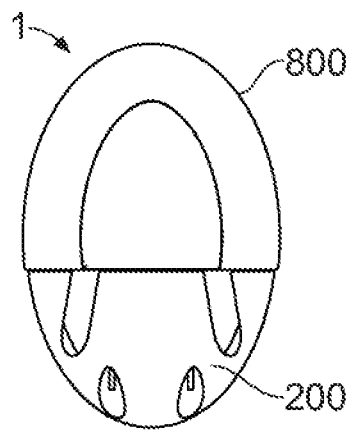
FIG. 26
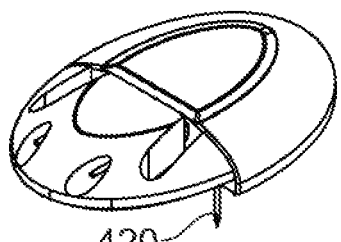
FIG. 27
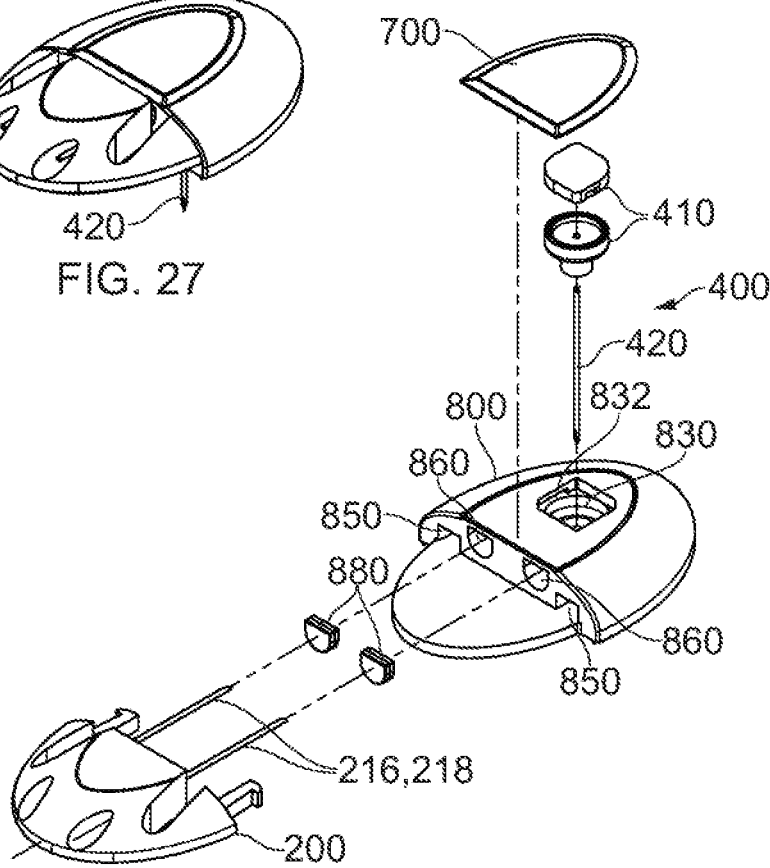
FIG. 28
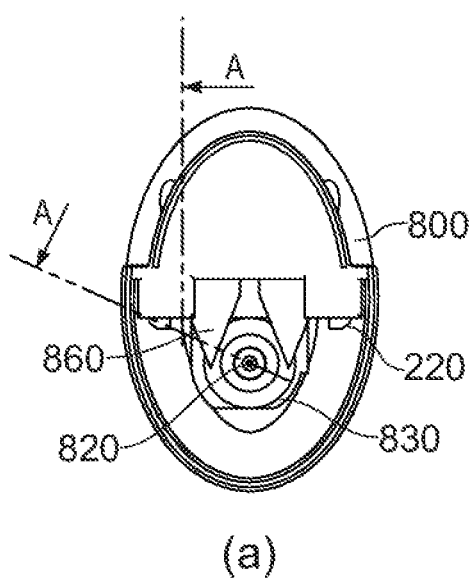
(a)
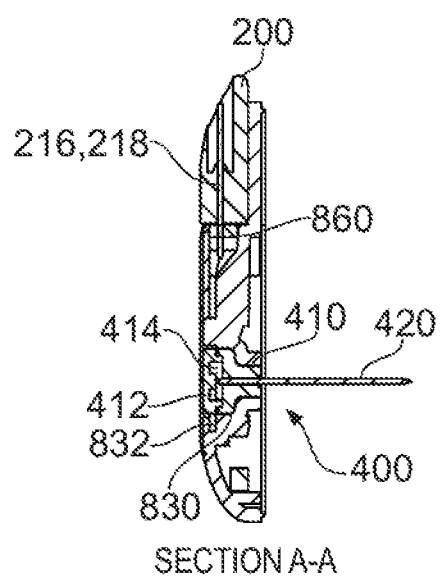
SECTION A-A
(b)
FIG. 29

SECTION A-A

SECTION C-C

CONNECTOR

This application is a continuation of International Application No. PCT/EP2020/077310 filed Sep. 30, 2020 and claims the priority of foreign application no. GB1914132.4 filed Oct. 1, 2019. The disclosures of which are hereby incorporated herein in their entirety.

FIELD

The present invention relates to a connector for an infusion set, and to an infusion set for administering multiple fluids to a patient. The infusion set may comprise the connector of the invention. Also provided is the use of the connector or the infusion set for sub- or trans-cutaneous administration of at least two independent fluids (e.g. medicaments, hormones or the like) to a patient in need thereof, and a method of sub- or trans-cutaneously delivery of at least two independent fluids to a patient in need thereof.

BACKGROUND

Infusion sets are well-known in the art. They usually include a base which is adhered to te skin of a patient, a penetrating member such as a needle or cannula which is inserted into the patient's subcutaneous tissue, and a connector for attaching a pump to the base so that fluid can be subcutaneously administered either intermittently or continuously to the patient.

Typically, however, it is only possible to administer one fluid at a time via a single infusion set. Should a patient need to administer more than one fluid independently (e.g. multiple medicaments, hormones or the like which are not in the form of a mixture), they have to use more than one infusion set, each with its own base, penetrating member and connector. This causes severe issues with patient compliance since it is burdensome and uncomfortable for a patient to apply and use more than one infusion set. Not only does the patient have to identify different injection sites for each infusion set to avoid complications, but they have to self-administer more than one injection and ensure that the same fluid is administered via each infusion set on each use.

Numerous actives, e.g. drugs, hormones or the like are administered subcutaneously. The selection of subcutaneous administration can be for example, to avoid contact with substances in the mouth or stomach which may cause degradation following oral administration (e.g. acid and certain enzymes), to avoid difficulties and cost that can be associated with other methods like intravenous injection, and/or enable rapid administration times. For small amounts of sensitive actives, a subcutaneous injection can be a useful, safe and convenient method of administering the substance to a patient. Examples of subcutaneously administered substances are therefore extensive, and include epinephrine to quickly treat severe allergic reactions, pain medications such as morphine and hydromorphone, and nausea and vomiting medicaments such as metoclopramide or dexamethasone, amongst others. Combinations of drugs, hormones or the like may also be administered subcutaneously because of these same advantages.

Multiple actives may, for example, be used simultaneously or sequentially to treat a particular therapeutic condition or two closely-linked conditions. Simultaneous use and sequential use requires, however, that the actives do not react with one another when administered to a patient, which for certain actives is unavoidable and can in some circumstances (e.g. with antagonistic combinations) be problematic for the patient. Combinations of actives may, for example, have a counterbalancing effect meaning that any mixing thereof reduces the positive therapeutic effect of either active on the patient.

An example of where administration of multiple actives is vital but problematic is in the management of diabetes. Diabetes is a chronic condition in which a person has elevated blood glucose levels that result from defects in the body's ability to produce and/or use insulin. There are three main types, and insulin is used to control blood sugar in people who have Type 1—where the body does not produce insulin—or Type 2—where the body does not produce or use insulin normally. Occasionally, however, the amount of dosed insulin can be too high leading to hypoglycemia or a situation of impending hypoglycemia. To combat and/or reverse such adverse situations, individuals can administer a so-called "rescue-dose" of a counter insulin regulatory agent, such as glucagon. Glucagon and insulin are antagonistic hormones and so should typically not come into contact with each other in order to have their desired effect.

WO2017/007968 describes an infusion set for delivering one or multiple medicaments to a patient.

SUMMARY

There is a need in the art for a single infusion set which enables multiple, but independent fluids to be subcutaneously administered to a patient. Such an infusion set would improve comfort and convenience for the patient, reduce the amount of hardware the patient has to wear on their body and the number of needles required for use. The infusion set should avoid any interaction between fluids before they enter the body, and be simple for patient use, understanding and compliance. Furthermore, it would be advantageous for an infusion set to enable independent control of each of the fluids being administered such that replacement of one fluid does not disturb administration of another.

According to the first aspect of the present invention, there is provided a connector for an infusion set. The connector includes a body having a first portion and a second portion, and at least one arm. The at least one arm is connected to the body and configured to couple with a base of an infusion set. The first portion and second portion of the body are configured to be removably and replaceably coupled together, and each has a fluid delivery conduit which is configured to allow fluidic communication of the connector with a different or at least two independent fluid sources (e.g. via a pump or the like). For example, the fluid delivery conduit of the first portion is configured to allow fluidic communication with a first fluid source, and the fluid delivery conduit of the second portion is configured to allow fluidic communication with a second fluid source, the first and second fluid sources containing different fluids.

In various embodiments of the present invention, each fluid delivery conduit defines an independent fluid path. In various embodiments, the fluid delivery conduits are configured to allow fluidic communication of the connector with two to four, two to three, or two independent fluid sources.

In various embodiments of the present invention, the connector further includes one or more guide members. Such guide members are configured to aid coupling of the connector with the base of the infusion set, and may extend from the body of the connector. In terms of shape and/or size, the guide members are not particularly limited, as long as they fulfil their desired function. As an example, however, the guide members may have a substantially uniform cross-section.

In various embodiments of the present invention, the connector further includes at least two penetrating elements, for example, two to four, two to three, or two penetrating elements. These penetrating elements may be located on the body of the connector, and may, for example, be coupled to and extend from the body of the connector to facilitate coupling of the connector to an infusion set. In various embodiments of the present invention, each penetrating element is associated with one of the fluid delivery conduits, and each penetrating element extends from the body of the connector. In various embodiments, the at least two penetrating elements are in fluidic communication with the at least two independent fluid sources via the fluid delivery conduits.

In various embodiments of the present invention, the at least one arm extends from the body of the connector. The connector may, for example, include at least two arms, extending from each respective portions of the connector body. In terms of shape and/or size, the arm(s) is not particularly limited, provided that it fulfils its function of coupling the connector to a base of an infusion set. In various embodiments, the arm has a non-uniform cross-section and a coupling means for connecting with the base of the infusion set. Such coupling means may be at the distal end of the arm. In various embodiments, the coupling means comprise a hooked end or an inclined surface; on coupling with the base of the infusion set, the hooked end or inclined surface will generally be pushed inward by a feature on the base (e.g. a protrusion or other surface feature) and thereby couple or engage with the infusion set (e.g. via an aperture or other surface feature in the base).

In various embodiments of the present invention, the first and second portions are connected with or via complementary surface features. In one arrangement, the first portion may have one or more protrusion or rib extending outwardly from a surface, and the second portion may have one or more complementary groove or recess formed within a surface. In an alternative arrangement, the second portion may have one or more protrusion or rib extending outwardly from a surface, and the first portion may have one or more complementary groove or recess formed within a surface. Other arrangements may have a combination of protrusions or ribs and complementary grooves or recesses on the first and second portion of the connector body.

Alternative arrangements may involve the surface feature associated with the first portion being a rail type element and the surface feature associated with the second portion being a channel that is sized and configured for receiving and reversibly coupling with the rail type element. The shape or cross-section of the rail type element is not limited; it may be rectangular, triangular, cylindrical, semi-cylindrical, tapered or the like.

In various embodiments of the present invention, the first and second portions are connected with or via complementary male and female parts. The male part may take the form of an outward extension or projection from the respective portion, and the female part may take the form of an inward groove, recess or slot. The groove, recess or slot may have a neck or narrower cross-section towards the edge of the groove/recess/slot, e.g. a lip or raised edge. The groove, recess or slot may further include a wall at the distal end thereof. In various embodiments, the male and female parts form a bayonet connection.

In various embodiments of the present invention, the first and second portions are configured to be coupled together along at least a portion of the length of the body. In various embodiments, the first and second portions are configured to be coupled together along at least a portion of the length of the fluid delivery conduits.

According to the second aspect of the present invention, there is provided an infusion set for administering multiple fluids to a patient. The infusion set includes a base, an insertion portion, and a connector. The base may be used to secure the infusion set to the skin of a patient (e.g. at a placement site) and thus includes an adhesive portion. The base also includes a hub configured to couple with the connector and at least one lumen configured to receive the insertion portion. The insertion portion has at least one penetrating element for supplying fluid to the infusion placement site, where the penetrating element(s) is coupled to and extends from the base. The at least one penetrating element is configured to administer the multiple (i.e. at least two independent) fluids sub- or trans-cutaneously to the patient. The connector is coupled to the base and has a body, at least one arm and at least two fluid delivery conduits. The at least one arm is connected to the body and configured to couple with the hub of the base. The fluid delivery conduits are configured to allow fluidic communication between at least two independent fluid sources and the at least one penetrating element.

In various embodiments of the present invention, the connector included in the infusion set is a connector of the present invention as defined herein.

In various embodiments of the present invention, the infusion set has two or more insertion portions. With two or more insertion portions, the base has two or more lumens, each lumen independently configured to receive a respective insertion portion. The two or more insertion portions respectively define two or more fluid paths from the at least two independent fluid sources via the fluid delivery conduits of the connector to the infusion placement site.

In alternative embodiments of the present invention, the infusion set has a single or one insertion portion. In this arrangement, the base has a lumen configured to receive the insertion portion and the insertion portion has at least one penetrating element connected to and extending from a housing. The housing of the insertion portion has at least two chambers configured to allow fluidic communication between at least two independent fluid sources and the at least one penetrating element. The at least two chambers are independent from each other, thereby preventing the multiple fluids from coming into contact with each other.

The base with the single lumen may further have at least two openings which substantially align with the at least two chambers of the housing, and are configured to allow fluidic communication with the at least two independent fluid sources. This arrangement advantageously allows a fluid path to be formed from a first fluid source to the infusion placement site, and a separate fluid path from a second fluid source to the infusion placement site. The fluid paths run independently of each other, preventing the fluids from coming into contact with each other. As part of these fluid paths, each of the chambers of the insertion portion housing may have an opening for fluidic communication with the at least one penetrating element, and an opening for fluidic communication with one of the fluid delivery conduits of the connector.

In various embodiments of the present invention, the chambers of the housing are spaced apart from each other. There may, for example, be an intermediary wall or other feature separating the chambers, thereby preventing the fluids from mixing inside the insertion portion.

In various embodiments of the present invention, the at least one penetrating element comprises a piercing member (e.g. a needle or the like) or a self-penetrating cannula. In various embodiments, the at least one penetrating element comprises a multi-lumen cannula. Such a multi-lumen cannula may have a first lumen with a distal end for fluid communication between the placement site and a first fluid source, and a second lumen with a distal end for fluid communication between the placement site and a second fluid source. The first and second lumens, in a similar manner to the first and second chambers, are independent from each other to prevent fluid mixing. In various embodiments, the distal end of the first lumen is spaced apart from the distal end of the second lumen. In alternative embodiments, the first lumen is an outer lumen and the second lumen is an inner lumen, or the first lumen is an inner lumen and the second lumen is an outer lumen.

In various embodiments of the present invention, the multi-lumen cannula comprises a piercing member between a first lumen and a second lumen, where both lumens run along the length of the cannula and are separate (independent) from each other. In various embodiments, the proximal end of the penetrating element may be a notched end or include a notch.

In various embodiments of the present invention, the infusion set further comprises a sensor portion. The sensor portion may be any sensor arrangement known in the art. The sensor portion may have at least one sensor extending from the base which is configured for determining at least one body characteristic of the patient (e.g. blood glucose). In various embodiments, the sensor portion may comprise a lumen in the at least one penetrating element (e.g. the multi-lumen cannula defined herein) for the at least one sensor. For example, the sensor may run along a central lumen and the cannula may include an additional two lumens for the two fluids to be administered, i.e. be in the form of a tri-lumen cannula. The sensor portion may further comprise a groove in the insertion portion housing and a groove in the base.

In various embodiments of the present invention, the infusion set further comprises a cap for coupling with the base. The cap may have tracks on its inside surface (i.e. the surface not exposed to the user) for coupling with the base. In various embodiments, the base has at least two channels configured to allow fluidic communication with the at least two independent fluid sources, and the cap has at least one track on its inside or inner surface for coupling with said channels. The at least one track for coupling with the housing may be formed of a membrane material, e.g. a silicone rubber or the like.

According to the third aspect of the present invention, there is provided the use of the connector defined herein in an infusion set for sub- or transcutaneous delivery of at least two independent fluids to a patient in need thereof.

According to the fourth aspect of the present invention, there is provided the use of the infusion set defined herein for sub- or trans-cutaneous delivery of at least two independent fluids to a patient in need thereof.

According to a fifth aspect of the present invention, there is provided a method for sub- or trans-cutaneously delivering at least two independent fluids to a patient in need thereof. The method comprises providing an infusion set as defined herein, placing said infusion set on the skin of a patient, connecting each fluid delivery conduit of the connector to at least two independent fluid sources, and delivering said at least two independent fluids to the patient. In various embodiments, the connector may be as defined herein according to the present invention.

In various embodiments of the third, fourth and fifth aspects at least one of the fluids comprises a first active, e.g. a first drug or a first hormone, and/or at least one of the fluids comprises a second active, e.g. a second drug or a second hormone. For example, at least one of the fluids may comprise insulin and/or at least one of the fluids may comprise glucagon. In such exemplary embodiments, the connector and/or infusion set are useful in insulin therapy and diabetes management. Equally, at least one of the fluids may comprise a pain medication such as morphine or hydromorphone, and/or at least one of the fluids may comprise a nausea or vomiting medicament such as metoclopramide or dexamethasone.

These embodiments are set out in the appended independent and dependent claims. It will be appreciated that features of the dependent claims may be combined with each other and with features of the independent claims in combinations other than those explicitly set out in the claims.

Furthermore, the approaches described herein are not restricted to specific embodiments such as those set out below, but include and contemplate any appropriate combinations of features presented herein. For example, a connector, infusion set, use and/or method may be provided in accordance with approaches described herein which includes any one or more of the various features described below as appropriate.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principals of the invention, and although not to scale, show relative dimensions.

FIG. 4(a) is a front view showing the position and cross-section of arms 120 and guide members 130, along with fluid delivery conduits 116 and 118 of the first and second body portions respectively. FIG. 4(b) is a side view showing the relative lengths and side-profile of the arm 120 and guide member 130. FIG. 4(c) is a back view showing the coupling between the first portion 112 and second portion 114 and the fluid delivery conduits 116, 118.

FIG. 7(a) is a schematic end view showing an alternative coupling of first 112 and second 114 portions. FIG. 7(b) is a schematic top view. FIG. 7(c) is a schematic front view showing the alternative coupling of first 112 and second 114 portions. FIG. 7(d) is a side view showing the relative lengths and side-profile of the arm 120 and guide member 130.

FIG. 10 includes views (a), (b) and (c) of a connector 100 in accordance with another embodiment of the invention. FIG. 10(a) is a top view of connector 100 showing de-coupling of a male connector part 154 and a female connector part 164. FIGS. 10(b) and 10(c) are end views of the connector of FIG. 10(a) showing the cross-section of the male and female connector parts.

FIG. 11 includes views (a) and (b) of the second portion 114 of the connector in FIG. 10. FIG. 11(a) is a perspective view showing the female connector part 164. FIG. 11(b) is an end view of the second portion 114 in FIG. 11(a).

FIG. 12 includes views (a) and (b) of the first portion 112 of the connector in FIG. 10. FIG. 12(a) is a perspective view showing the male connector part 154. FIG. 12(b) is an end view of the first portion 112 in FIG. 12(a).

FIG. 13 is a side view of connector 200 in FIG. 14 in accordance with another embodiment of the invention.

FIG. 14 is a perspective view of connector 200 showing cannula holes or fluid delivery conduits 216, 218.

FIG. 15 is a cross-sectional view of the end of connector 200 in FIG. 14.

FIG. 16 is a schematic view of the top of connector 200 in FIG. 14 showing hooked ends 222 of arms 220.

FIG. 17 includes a cross-sectional view along line A-A showing fluid delivery conduits 216, 218.

FIG. 24(a) is a perspective view of the base showing single lumen 830, FIG. 24(b) includes cross-sectional views A-A and B-B of the base and FIG. 24(c) is a side view of the hub 820.

FIG. 25(a) is a bottom view showing the shape of channels 860, and the underside of lumen 830. FIG. 25(b) is a side view, FIG. 24(c) is a top view and FIG. 24(d) is an end view.

FIG. 26 is a top view of an infusion set 1 in accordance with another embodiment of the invention.

FIG. 27 is a perspective view of the infusion set in FIG. 26 showing penetrating element 420 extending from the base.

FIG. 28 is an exploded perspective view of the infusion set in FIG. 26 showing how the connector 200 couples with base 800, and how the insertion portion with cannula 420 and housing 410 is positioned in the single lumen 830 and is sealed by cap or cover 700.

FIG. 29(a) is a bottom or underside view of a base 800 in accordance with an embodiment of the invention. FIG. 29(b) is a cross-sectional view along A-A of FIG. 29(a) showing chambers 412, 414 inside the cannula housing.

FIG. 32(a) is a side view of the single lumen base 800 showing where cross-sectional view A-A was taken for FIG. 32(b). FIG. 32(b) shows the fluid paths formed by channels 860 in the base 800.

FIG. 33(a) is a perspective view of a tri-lumen insertion portion 300 showing sensor groove 340 in the top of the housing 330 and a dotted line for the sensor path through a tri-lumen cannula 320. FIG. 33(b) includes side views of the cannula showing sensor groove 340 and chamber entrances 316 in the same manner as FIG. 31(b).

FIG. 34 includes two cross-sectional views.

FIGS. 36(b) and (c) are side views of the base and FIG. 36(a) is a top view showing groove 870. Groove 870 can also be seen in FIG. 36(d), a perspective view of the base 800 for an infusion set 1 comprising a sensor portion. FIG. 36(e) is a side view of the front of the base 800 showing channels 860 for coupling with the fluid delivery conduits of a connector and groove 870 of the sensor portion.

FIG. 38(a) is of a base 800 containing insertion portion (not shown in detail) and cap 700 in accordance with an embodiment of the invention. FIG. 38(b) includes a cross-sectional view A-A across the channel 860 of the embodiment of FIG. 38(a), and an exploded view of the same embodiment. FIG. 38(c) includes a cross-sectional view B-B across the underside of the base, and an exploded view of the same embodiment showing the relationship between tracks 720 on the underside of the cap 700 and the housing 310 of the insertion portion 300 to form independent fluid paths.

DETAILED DESCRIPTION

Features of certain examples and embodiments are discussed and described herein. Some features of certain examples and embodiments may be implemented conventionally and these are not discussed or described in detail in the interests of brevity. It will thus be appreciated that features of apparatus, uses and methods discussed herein which are not described in detail may be implemented in accordance with any conventional techniques for implementing such features.

Unless otherwise defined, all terms of art, notations and other scientific terms or terminology used herein are intended to have the meanings commonly understood by those of skill in the art to which this invention pertains.

As shown in the accompanying figures for purpose of illustration, the invention is embodied in a connector for use in an infusion set, and an infusion set for subcutaneously delivering a plurality of fluids without contamination or mixing thereof, to a patient. Specific examples are set out below with respect to a dual-fluid delivery and infusion system. However, the skilled person will readily recognize that the connector and infusion set of the present invention may be used, configured or designed to deliver more than two independent fluids. Accordingly the invention is not limited in this respect.

With a conventional connector and infusion set suitable for delivering a single type of fluid to a patient (e.g. in a conventional infusion system), it is unnecessary to be able to monitor and independently control the administration of multiple fluids. Because the conventional system utilizes only a single fluid, there is specifically no need to avoid mixing or contamination of fluids, or permit replacement of one fluid without disturbing the administration of another. These issues only arise when multiple, independent fluids are to be delivered or infused within a patient. This is especially the case with counter-acting fluids such as glucagon and insulin, since any contamination or lack of independent fluid control can be harmful or potentially fatal.

The present invention addresses these and other problems. Exemplary embodiments provide a safe and reliable multi-fluid infusion system that prevents fluid contamination, and in some instances allows independent fluid control. The apparatus, methods and uses of the present invention can therefore be used in an in-patient setting or an out-patient setting. Additionally they can be used as an autonomous or semi-autonomous closed-loop system for controlling one or more body characteristic, e.g. glucose.

Figure 1:
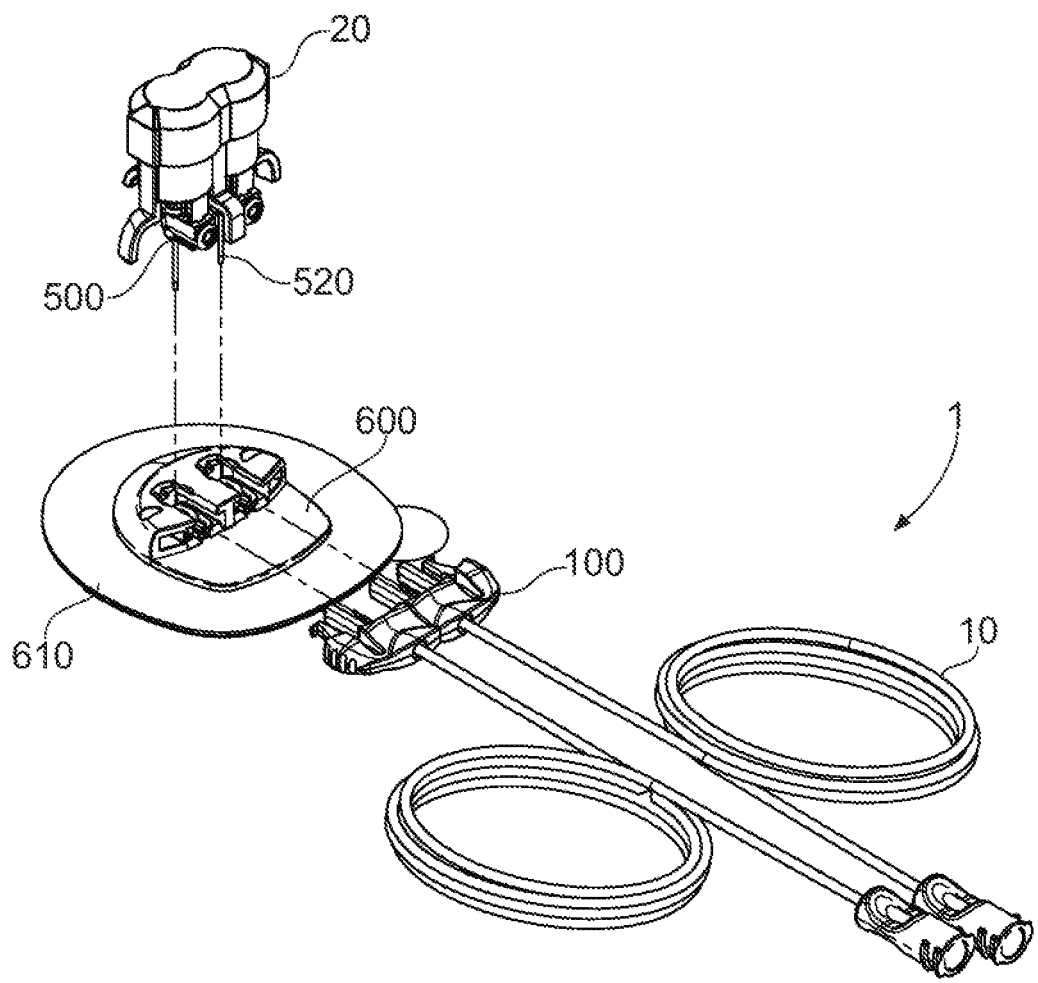
FIG. 1 is a perspective view of an exemplary multi-fluid infusion system 1 having tubing 10 to connect to an infusion pump (not shown), a connector 100 according to an embodiment of the invention, a base 600 with an adhesive portion in the form of "peel-off" paper, and an inserter containing dual insertion portions 500 for coupling with the base.

FIG. 1 is a diagram depicting an overview of a multi-fluid infusion system 1 according to an exemplary embodiment of the present invention. The illustrated infusion system 1 includes two separate tubes 10 for attachment to, for example, a delivery device such as an infusion pump (not shown) for delivering two, independent (i.e. separate) fluids to a patient. The system 1 includes a connector 100 according to an exemplary embodiment of the present invention, which fluidly couples tubes 10 to base 600 and infusion portion 500 in order to sub- or trans-cutaneously deliver both fluids to a patient. The coupling of the connector to the base is shown with dotted lines in FIG. 1. The combination of the base 600, infusion portion 500 and connector 100 is referred to herein as an infusion set 1. As will be understood by the skilled person, the shape of the infusion set and/or connector according to the present invention is not limited. The infusion set may, for example, be rectangular, circular, square, triangular, trapezoidal, octagonal or any other suitable shape known in the art.

Base 600 includes an adhesive portion 610 which in the embodiment of FIG. 1 is an enlarged pad having an underside surface coated with a suitable pressure sensitive adhesive. The base may come in any shape or size including, but not limited to, rectangular, circular, square, triangular, trapezoidal, octagonal or any other suitable shape known in the art. As can be seen in FIG. 1, a "peel off" paper may be provided to cover and protect the adhesive layer until the infusion set is ready for use. In alternative embodiments, the base may be affixed to a suitable adhesive material that can hold the infusion set to the body.

Base 600 can be seen in FIG. 1 to receive an insertion portion 500 from an inserter 20. The inserter is not within the scope of the present invention, and any suitable inserter for a medical device as known in the art may be used. Dotted lines in FIG. 1 show how the insertion portion 500 with penetrating elements 520 couples with the base 600; the features of the base 600 and insertion portion 500 are discussed in more detail below.

In use, the peel-off paper may be removed from the pad at which time the base 600 can be pressed onto and seated upon the patient's skin. An inserter 20 may then be used to insert the penetrating element(s) 520 of the insertion portion 500 at the selected infusion placement site within the body of the patient. As is typical for infusion sets in the art, if the penetrating element(s) 520 includes a cannula together with a piercing member (e.g. a metal needle), insertion of the element(s) may leave the cannula in place within the body of the patient whilst the needle is withdrawn from the patient. The cannula may be left in the trans-cutaneous or sub-cutaneous tissue of the patient. Alternatively if the penetrating element(s) 520 is a self-penetrating cannula as known in the art, insertion of the element(s) may be achieved with the cannula itself, a separate piercing member may not be necessary. Tubing such as 10 may then be used to fluidly couple connector 100 with an infusion pump, and multiple fluids independently administered from the pump via the connector 100 and penetrating element(s) 520 of insertion portion 500, to the patient.

Figure 2:
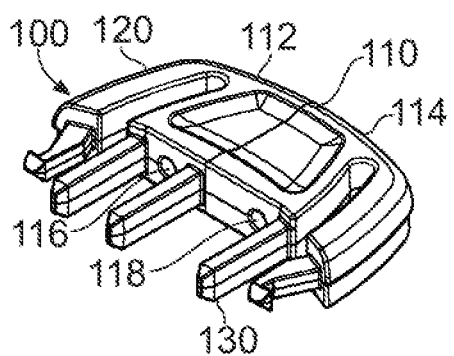
FIG. 2 is a perspective view of a connector 100 in accordance with an embodiment of the invention showing the division of the body into a first portion 112 and a second portion 114.
Figure 3:
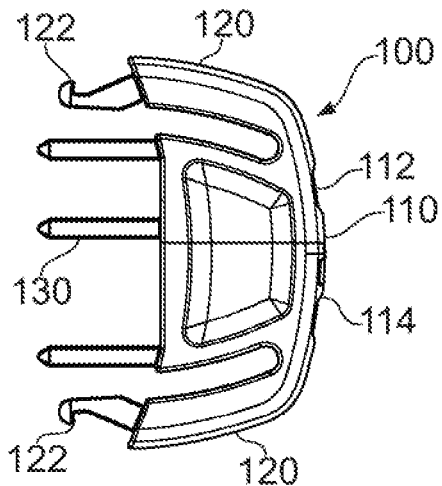
FIG. 3 is a top view of the connector 100 of FIG. 2.
Figure 6:
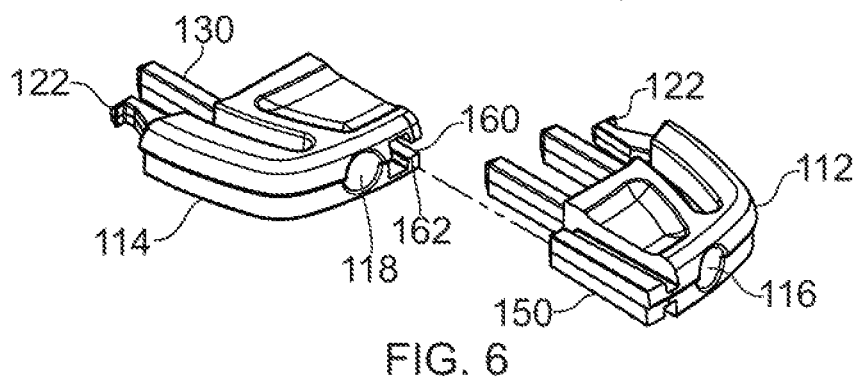
FIG. 6 is a perspective view of the connector 100 of FIG. 2 when the first portion 112 and second portion 114 have been de-coupled; coupling is via a substantially rectangular rail or rib 150 on the first portion and a complementary recess 160 in the second portion.
Figure 7:
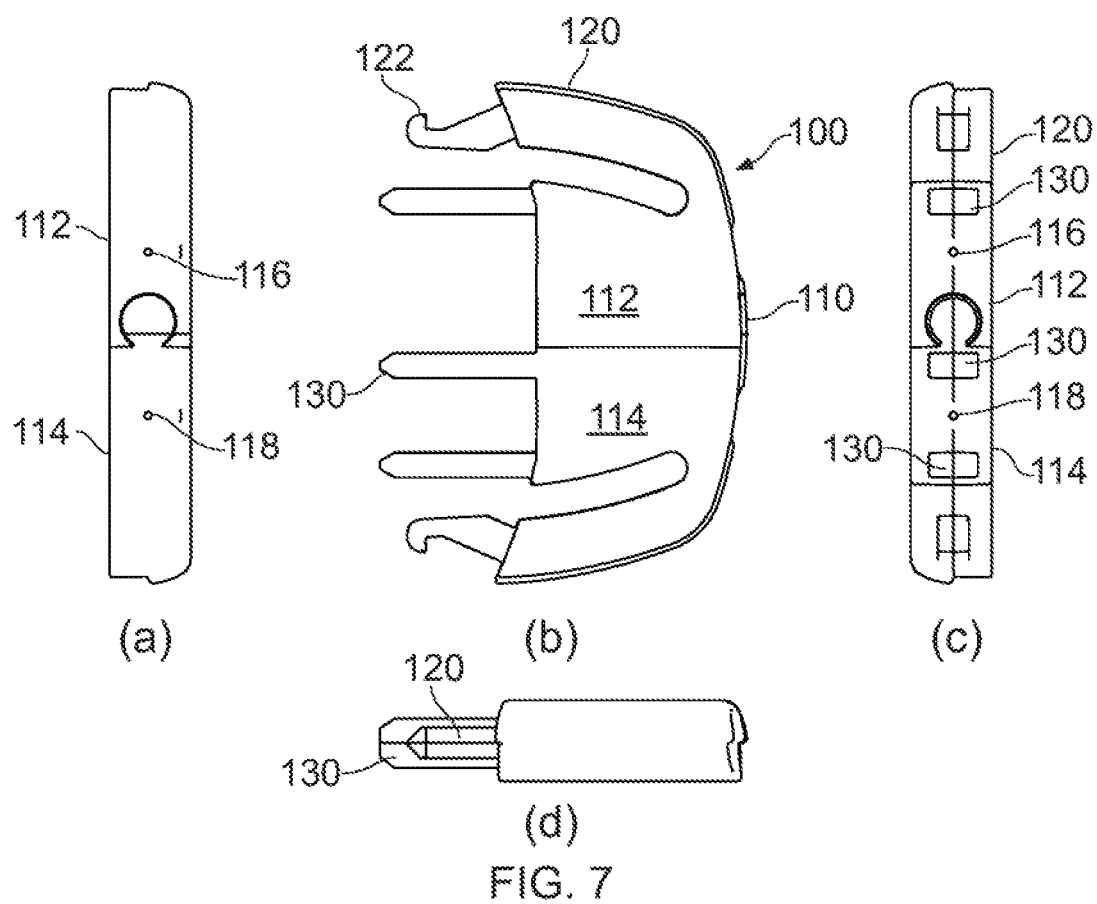
FIG. 7 contains views (a), (b), (c) and (d) of the connector 100 of FIG. 8 in accordance with another embodiment of the invention.
Figure 8:
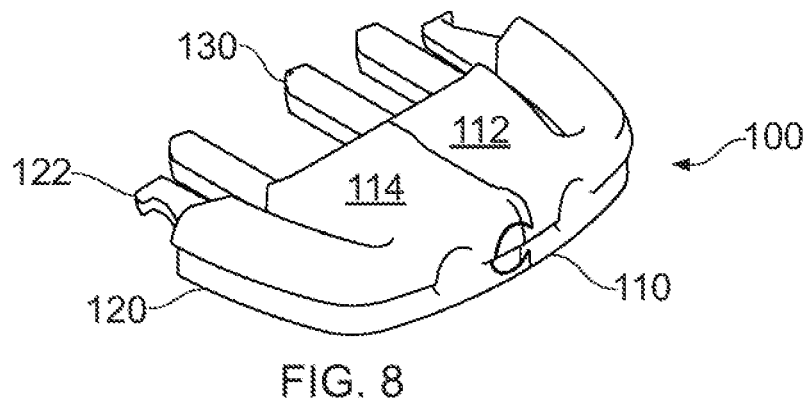
FIG. 8 is a perspective view of connector 100 in accordance with another embodiment of the invention.

FIGS. 2 to 9 relate to a connector 100 according to an exemplary embodiment of the invention. FIGS. 2 and 8 are perspective views of the connector 100, both showing how the connector has a body 110 divided into two portions 112, 114. In both FIGS. 2 and 8, the body 110 is approximately divided along its centre line so that the first and second portions are of approximately equal size. The invention is not, however, limited to such a division and the skilled person will appreciate that the division of the body may be off-centre, such that one portion is larger than the other. Such an embodiment may be useful where one fluid is administered at a larger volume than the other fluid. Alternatively, a larger portion may be used for separate administration of two fluids (e.g. via two fluid delivery conduits in said portion), and the smaller portion then used for administration of a third fluid (e.g. via a third fluid delivery conduit in said portion).

Figure 4:
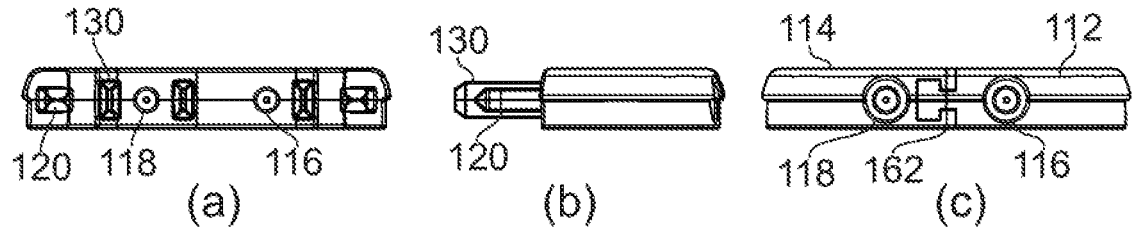
FIG. 4 contains views (a), (b) and (c) of the connector 100 of FIG. 2.

As illustrated by FIGS. 2, 4(*a*), 4(*c*) and 6, the fluid delivery conduits 116, 118 may run along the length of the body of the connector, and thereby bridge the span between the tubing 10 shown in FIG. 1 to the fluid delivery device (e.g. infusion pump), and the base of the infusion set. Each conduit 116, 118 forms an independent channel with an end proximal to the fluid delivery device and a distal end towards the base of the infusion set. Each conduit may further be a single or multiple-lumen conduit. The conduits may be joined by webbing or some other manner, or may be completely separate from one another in the connector body. In the context of the invention, the fluid delivery conduits typically form independent fluid paths.

Figure 9:
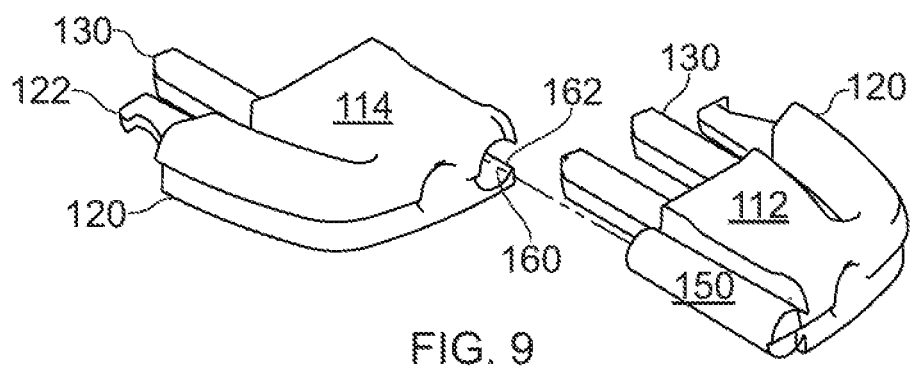
FIG. 9 is a perspective view of the connector 100 of FIG. 8 when the first portion 112 and second portion 114 have been de-coupled, showing how the coupling is via a substantially cylindrical rib or rail 150 along the length of the first body portion and a complementary recess 160 in the second portion.
Figure 18:
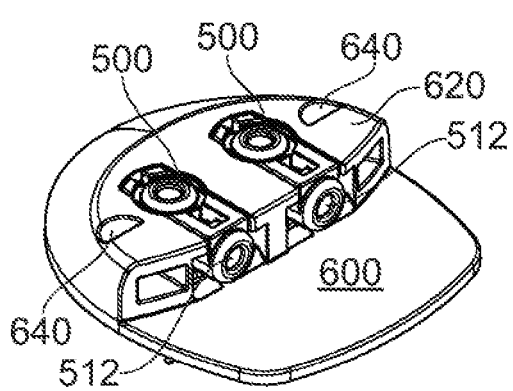
FIG. 18 is a perspective view of a dual-lumen base 600 and dual insertion portion 500 for an infusion set according to an embodiment of the invention.
Figure 19:
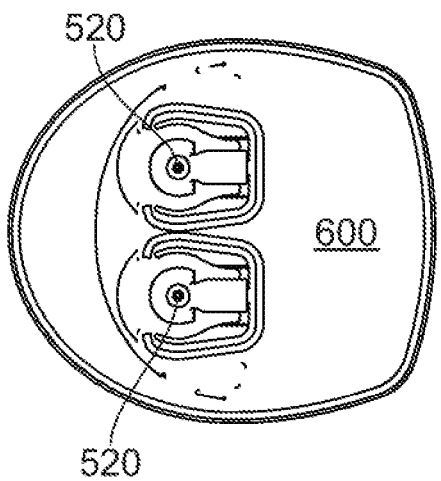
FIG. 19 is a bottom view of the base and insertion portion in FIG. 18 showing penetrating elements 520 of insertion portions 500.

It can be seen from FIGS. 6 and 9 how the first and second portions 112, 114 are configured to be removeably and replaceably coupled together. By the expression "removeably and replaceably coupled" is meant that the portions can be repeatedly coupled and uncoupled together in order to assist the patient in assembling and using the connector. Advantageously the coupling of the first and second portions 112, 114, may enable the patient to remove one portion without the other when the connector is coupled to the base 600 during normal use. Alternatively, the patient is able to uncouple the portions after the connector 100 has been removed from the base 600. The ability to repeatedly couple and decouple the connector via first and second body portions 112, 114 allows the patient significant flexibility in using the connector in an infusion set since the patient can replace one or both fluids as needed.

The first and second portions of the body 112, 114 can be formed of any suitable material, including metals and non-metals. The metal may be spring steel or a similar material. Spring steel is a term used in the art to refer to those steels used in the manufacture of springs, prominently in automotive and industrial suspension applications. Such steels are generally low-alloy manganese, medium-carbon steel or high-carbon steel. Suitable non-metals include thermoplastics such as polypropylene, poly(methyl methacrylate), acrylonitrile butadiene styrene, polyamides, polylactic acid, polybenzimidazole, polycarbonates, polyetherether ketone, and polyethylenes. Typically the first and second portions of the body are formed from polypropylene.

It can be seen from FIGS. 2, 3, 5, 6, 7(b), 8 and 9 how both first and second portions 112, 114 of the body can include arms 120, guide members 130 and fluid delivery conduits 116, 118. In the exemplary embodiment of these figures, both guide members 130, and arms 120 extend outwardly from the body 110. In addition, the guide members 130 are depicted as identical to one another, whereas the arms 120 are mirror-images of one another. FIGS. 4(a), 7(b) and 7(c) show further how guide members 130 may be spaced apart from each other in a non-uniform pattern, and located between arms 130, whilst FIGS. 4(b) and 7(d) show that each of the guide members 130 are longer than arm 120.

The invention is not, however, limited to this configuration, provided that the connector can be non-reversibly coupled to the base of an infusion set. There may, for example, only be one arm 120 on the body 110, acting to couple the connector to the base of an infusion set. Advantageously, there may be one arm 120 on each portion, as illustrated in these Figures. With an arm on each portion, each arm having an independent coupling means, a patient is able to de-couple one portion without the other thereby facilitating independent fluid control.

In various embodiments of the invention, there may be only arms 120 and no guide members 130. When there are arms 120 and/or guide members 130 on each portion 112, 114, these may be the same or different; arms and/or guide members may, for example, differ in the manner by which coupling takes place with a base 600 of an infusion set. Further, the arm(s) 120 may be longer or the same length as the guide members 130, and the arm(s) may be located between guide members 130

The coupling between the arm 120 and the base 600 is also not limited, and may rely on any known connection technique, including the use of snap fit features and the like. Similarly the coupling of the guide members 130 (when present) and base 600 is not limited, and may rely on complementary surface features as defined herein.

Figure 5:
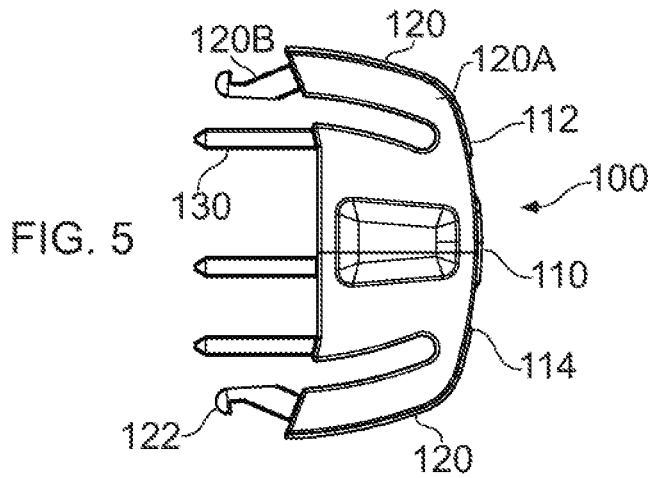
FIG. 5 is a bottom view of the connector 100 of FIG. 2.

In various embodiments of the present invention, the arms 120 are divided into two sections 120A, 120B as shown in FIG. 5, namely a distal section 120B (relative to the location of the infusion pump during use of the connector as shown in FIG. 1) and a proximal section 120A. In various embodiments, the arm 120 has at least two sections having a non-uniform cross-section there-between. In alternative embodiments, the arm 120 has a substantially uniform cross-section, similar to the guide members 130 seen in e.g. FIGS. 3 and 5.

For coupling with the base 600 of an infusion set, the arm 120 may have a "snap-fit" coupling means or rely on complementary surface features on the arm and base. A "snap-fit" coupling means may comprise a hooked end 122 as shown clearly in FIGS. 5 and 8, an inclined surface, or the like. It can be seen from e.g. FIG. 5 that the "snap-fit" coupling means 122 is found on the distal section 120B in this embodiment and takes the form of a hooked end.

With a "snap-fit" or surface feature coupling means on the arm 120, it will be understood by the skilled person that the base 600 of the infusion set will include corresponding features that will allow engagement of the connector 100 with the base 600. The corresponding features may be a cavity, groove, keyway, or slot to match with the "snap-fit" coupling means or a matching surface feature as defined herein.

For example, the "snap-fit" coupling means 122 may be compressed by the patient gripping the arms 120 of the connector 100 as they insert the connector 100 into the base 600, and this compression allows the coupling means 122 to slide over the corresponding feature in the base (e.g. the hub of the base). Once the connector is inserted all the way into the base 600, the release of the patient's grip allows the arms 120 and "snap-fit" coupling means 122 to re-expand and engage with the matching cavity, groove, keyway or slot in the base 600. This engagement can allow the connector 100 to be held in an appropriate position with little movement within the base 600.

The fluid delivery conduits 116, 118 are adapted to deliver a fluid to an appropriate inlet or channel on the base 600 of the infusion set. Although not shown in the FIGS. 2 to 9, the connector 100 may include at least two penetrating elements. Such penetrating elements may be located in the fluid delivery conduits 116, 118 and extend outwardly therefrom, e.g. in the same direction as the guide members 130. The penetrating elements can include any suitable structure configured to pierce or penetrate the insertion portion when mounted in the hub of the base so as to form a fluid passage from a fluid delivery device to the insertion portion. The penetrating elements may further be as defined below for those found in the insertion portion of the infusion set.

In various embodiments of the invention, the connector comprises at least two penetrating elements and an arm 120 extending outwardly from each portion 112, 114 of the body 110. Each arm 120 may comprise a coupling means 122 and the penetrating elements together with the coupling means of the arm may engage the connector with a base of an infusion set. With this configuration, it follows that the guide members 130 are optional.

As noted above, the advantageous removable and replaceable coupling between first and second portions 112, 114 is illustrated clearly in the exemplary embodiment of FIGS. 4(c) and 6. It can be seen from these figures, for instance, how the coupling may be over at least a portion of the length of the connector body 110. In various embodiments, the coupling may be over substantially the length of the connector body 110. This configuration results in a secure but divisible connector to ensure reliable and flexible fluid administration when used in a multi-fluid infusion set. Of note is that the coupling takes place at least in the region adjacent the base of the infusion set. That is, the infusion set does not require the connector to be coupled to a pair of separate and distinct administration regions that are spaced from each other. The patient only needs a single infusion set to receive delivery of multiple fluids.

The end view of FIG. 4(c) and exploded view of FIG. 6 shows how first portion 112 has a surface feature 150 which is received by a complementary surface feature 160 within second portion 114. The term "surface features" as used herein can include any suitable structure, coupler, connector, adapter or feature formed on, within or which protrudes from a surface of the respective portion having any suitable size, shape dimension, or element that allows, permits, enables or facilitates the coupling together of the body portions. Examples of suitable surface features include detents, ribs, slots, keys, grooves, holes, corrugations, indentations, or any other suitable mechanical coupling or attaching element. In some embodiments, the body portions may be indirectly coupled to each other through an intermediary coupling piece.

As illustrated in FIGS. 4(c) and 6, the first portion 112 can include a substantially rectangular rail-type surface feature 150 that is formed on and extends outwardly therefrom. Should, however, more than one surface feature be employed, these can be spaced apart and disposed at selected locations of the first portion 112. The second portion 114 then includes one or more complementary shaped surface features, such as for example groove or recess 160 that is formed within a surface opposing the first portion. Should more than one surface feature be employed, these are spaced at selected locations that correspond to the locations of the surface feature on the first portion. Hence, the second portion 114 having a groove or recess 160 formed therein is adapted to receive the corresponding rail 150 of the first portion 112.

The skilled person will readily recognize that many different types and shapes of surface features can be employed by the first and second portions 112, 114 of the present invention. The surface feature may also have a tapered cross-section to aid de-coupling and re-coupling of the connector. The skilled person will also recognize that the coupling can be reversed from that shown in FIGS. 4(c) and 6, e.g. with a rectangular rail-type surface feature 150 formed on and extending outwardly from the second portion 114 and the complementary groove or recess 160 formed within a surface of the first portion 112.

As illustrated in the end view of FIG. 4(c) and exploded view of FIG. 6, the surface feature formed within a portion of the body (here the second portion 114) may have a narrower cross-section (e.g. a neck) due to a lip or raised edge 162. This narrower cross-section may be along the length of the body, or may be along a portion of the length of the body, on the understanding that the shape of the groove/recess matches that of the surface feature on the other body portion. Advantageously lip or raised edge 162 facilitates removal of one portion without the other because of the ability of the patient to uncouple and detach the portion with the rail-type surface feature 150. FIG. 6 includes a dotted line showing the placement of the rail-type surface feature 150 in groove 160, and shows how one portion (here 112) can be removed without the other (here 114). This is a significant improvement over the connectors in the prior art and provides the patient with a marked flexibility for fluid delivery via an infusion set.

An alternative embodiment of the coupling between first and second portions 112, 114 is shown in FIGS. 7 to 9. The end views of FIGS. 7(a) and (c), together with the exploded view of FIG. 9 show how a substantially cylindrical rail-type projection 150 is formed on one portion (e.g. 112), and a complementary recess 160 is formed within the other portion (e.g. 114). The placement of the cylindrical rail 150 into the recess 160 is shown with a dotted line in FIG. 9. As in FIG. 6, the rail is formed along the length of the body but the invention is not limited to this configuration. Additionally, recess 160 has a lip 162 to facilitate the independent removal and replacement of each portion from one another. Corresponding features between FIGS. 2 to 6 and FIGS. 7 to 9 are labelled with the same reference numeral.

A further alternative embodiment of the coupling between first and second portions 112, 114 is shown in FIGS. 10, 11 and 12. The illustrated connector in FIG. 10(a) has a first portion 112 with a male connector part 154 (FIG. 10(c)) and a second portion 114 with a female connector part 164 (FIG. 10(b)). The male connector part 154 has a ribbed region 154A which is matched with internal grooves in the female connector part 164. Alternatively, the male connector part may have an external threaded region which is matched with an internal thread in the female connector part. The male and female coupling may be reversed such that the male connector part is on the second portion and the female connector part is on the first portion.

The male connector part 154 can be seen more clearly from FIGS. 12(a) and (b), and the female connector part 164 can be seen from FIGS. 11(a) and (b). In this exemplary embodiment, the female connector part 164 has an end wall 164A in the recess, which means that only the portion with the male connector part can be de-coupled and re-coupled whilst the connector is attached to a base of an infusion set. In certain embodiments, this removal mechanism is advantageous because it can be used by a patient or clinician to control which fluid is continuously administered. Insulin could, for example, be administered via the portion having the female connector part so that continuous administration was ensured, and glucagon could be administered via the portion having the male connector part because of the flexibility in its attachment and detachment to the infusion set.

Although not shown in the present Figures, one of the portions of the connector body may have a female portion of a bayonet style connector, coupled thereto. The corresponding feature element, such as a male portion of the bayonet style connector, can be coupled to the other respective body portion.

The connector of the present invention may be used in an infusion set, as seen in FIG. 1. The infusion set exemplified by FIG. 1 also includes base 600 with adhesive portion 610 and dual insertion portions 500. The base 600 of this exemplary embodiment is a dual-lumen base, illustrated in FIGS. 18 to 23.

Figure 22:
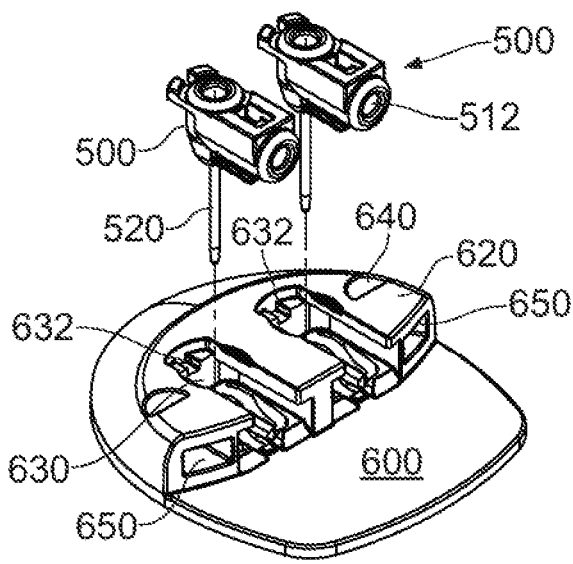
FIG. 22 is a perspective view of FIG. 18 showing how insertion portions 500 are positioned in dual lumens 630.
Figure 23:
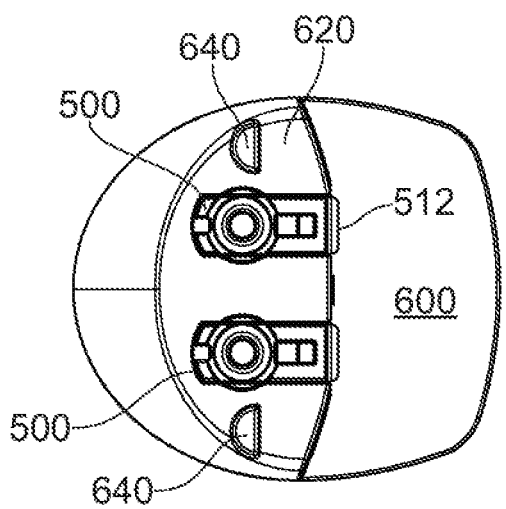
FIG. 23 is a top view of FIG. 18.

Base 600 is discussed above in relation to FIG. 1 in terms of its shape, size and an adhesive portion. FIG. 22, however, also shows that base 600 has a hub 620 and two lumens 630, each receiving a respective insertion portion 500. The placement of each insertion portion 500 in lumen 630 is shown by a dotted line in FIG. 22.

Hub 630 has apertures 640 formed therein so that the base may be coupled with a connector (not shown). In various embodiments of the invention, hub 630 comprises one or more complementary features for coupling with the connector, such as one or more apertures 640 for coupling with "snap-fit" coupling means, e.g. hooked ends 122, inclined surfaces or the like. The engagement of such coupling means with the base is detailed above and equally applies to the embodiment shown in FIGS. 18 to 23 as well as the embodiments discussed below. Along with apertures 640, the hub 630 may have apertures 650 for receiving the connector, e.g. for receiving the arms 120 of the connector 100.

The lumens 630 in the dual-lumen base 600 are not particularly limited, and may have any suitable surface features or the like for matching or engaging with complementary surface features of the insertion portions 500. The surface features may be as defined herein. FIG. 22 shows, for example, dents 632 in each lumen 630 which are shaped to mate with a complementary protrusion on the housing of the insertion portion (not shown).

As illustrated by FIGS. 18, 19, 20 and 23, the insertion portions 500 are received by lumens 630 such that they form a substantially flush fit therein and allow the penetrating element 520, such as a metal needle, a cannula or the like, to protrude from an underside or bottom surface of base 600. In addition, the engagement of the insertion portion 500 in lumen 630 facilitates a fluid pathway from port 512 of the insertion portion 500 to penetrating element 520.

Figure 20:
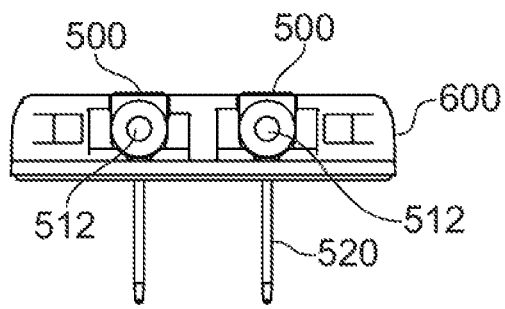
FIGS. 20 and 21 are schematic side-views of FIG. 18 showing the extension of penetrating elements 520 from base 600.
Figure 21:
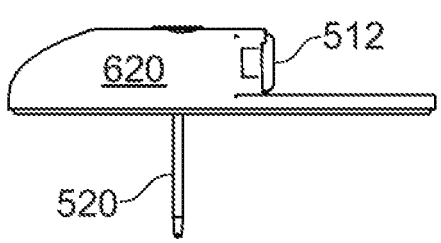

FIGS. 20 and 21 show, in particular how the penetrating element 520 protrudes from the bottom surface or underside of base 600. The penetrating element 520 can have different length, shape and/or profile depending on e.g. the fluid to be administered, patient characteristics etc. For example, the penetrating element 520 may include a hollow, solid, half or other fraction needle, having a diameter in the range of 18 gauge to 29 gauge or the like. This needle is typically formed from metal. Alternatively the penetrating element 520 may include a piercing member made out of non-metal materials, such as ceramic, plastic, composites, silicon microneedles, biodegradeable, hydrophilic substances, or the like.

In various embodiments of the invention, the penetrating element 520 includes a cannula; the cannula may be used with a metal needle or a non-metal piercing member or may be a self-penetrating cannula. The skilled person will be aware of suitable materials for the various penetrating elements, the self-penetrating cannula may, for example, be made from a thermoplastic such as those listed above for the material of the connector body portions, whilst the cannula used with a separate piercing member may be a soft, inert plastic material such as PTFE. When more than one penetrating element 520 is used, as shown in e.g. FIG. 20, these elements can be the same or different. Specifically, the elements can be formed of the same material, such as from metal or non-metal. Alternatively, the elements can be different and formed from different materials.

In another embodiment of the invention, there is provided an infusion set 1 as illustrated in FIGS. 26, 27 and 28. FIG. 26 shows how infusion set 1 includes base 800 and connector 200. The connector 200 in this exemplary embodiment is shown in more detail in FIGS. 13 to 17.

FIG. 14 is a perspective view of connector 200 showing how the connector of this embodiment of the invention has a body 210, arms 220 and fluid delivery conduits 216, 218. Arms 220 may be configured according to the embodiment described above in FIGS. 2 to 9; specifically, the arms may have a distal portion and a proximal portion, the distal portion having coupling means 222 for attaching the connector to a base of the infusion set. Coupling means 222 are shown in FIGS. 14, 16 and 17 as hooked ends, but they may take any form as detailed above and further form a "snap-fit" with the base 800 of an infusion set in the same manner as detailed above for the connector of FIGS. 2 to 9.

Connector 200 shown in FIGS. 13 to 17 may also have guide members (not shown) in the same manner as the connector of FIGS. 2 to 9.

FIG. 13 is a side view of the connector 200 in FIG. 14; FIG. 15 is an end view showing the end profile of fluid delivery conduits 216, 218. A cross-sectional view of such conduits (A-A) is shown in FIG. 17, and it can be seen from FIG. 17 how the conduits run along the length of the connector body, providing a fluid pathway through the body. It can also be seen from FIG. 17 how the conduits 216, 218 may have a non-uniform shape along their length. In alternative embodiments, the conduits may have a substantially uniform shape along their length, e.g. the conduits may be substantially tubular. The conduits may also form an array or be concentric with one another. The invention is not limited in this respect, provided that the conduits remain as independent channels for delivery of at least two independent fluids.

Figure 24:
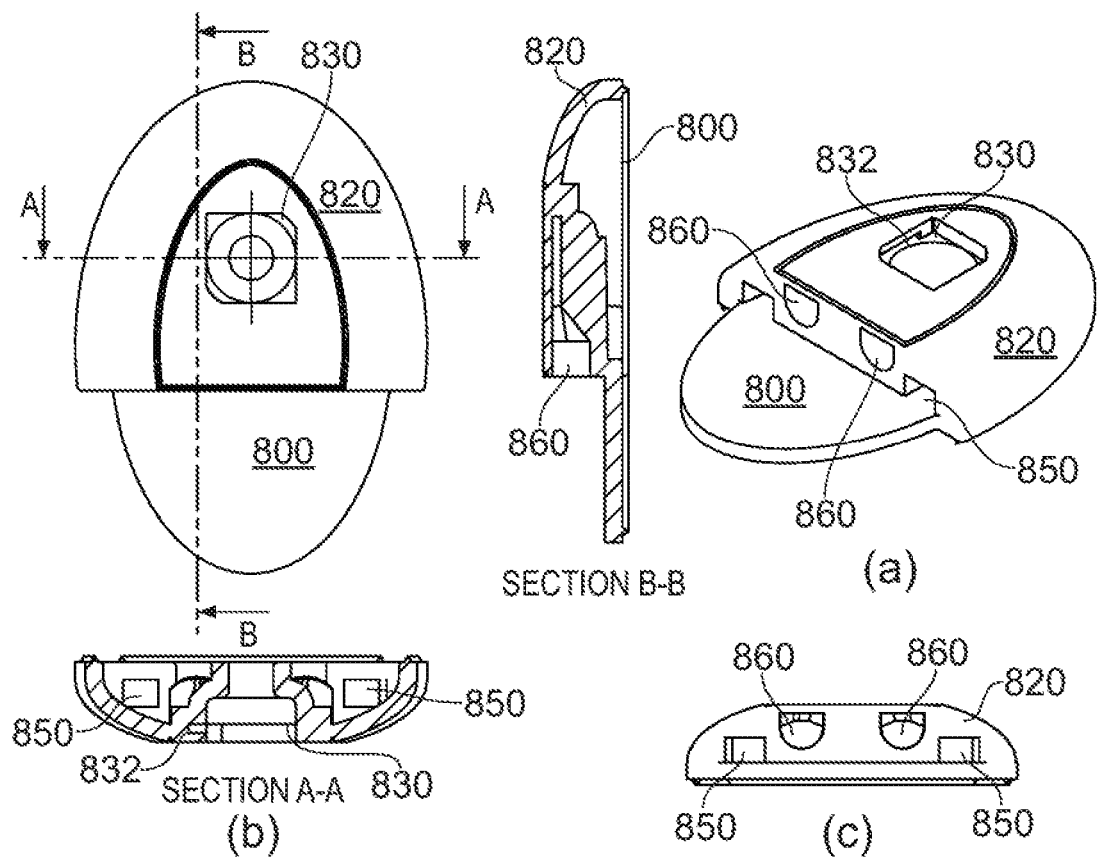
FIG. 24 includes views (a), (b) and (c) of a base 800 in accordance with another embodiment of the invention; namely a single-lumen base.
Figure 25:
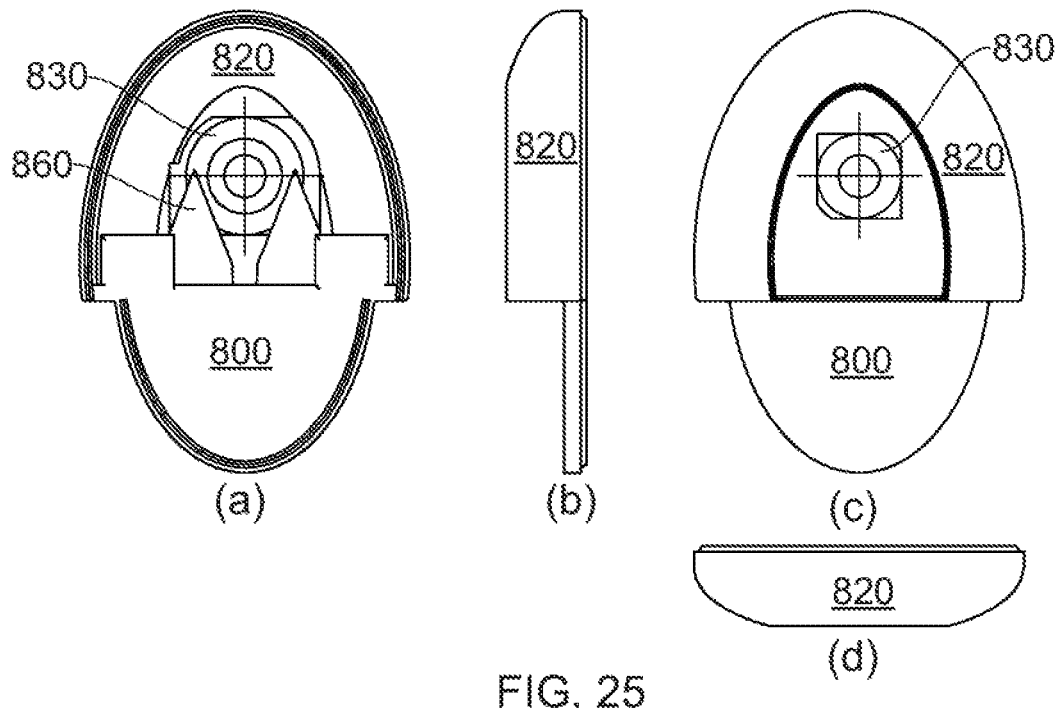
FIG. 25 includes views (a), (b), (c) and (d) of the base of FIG. 24.

An exemplary embodiment of base 800 from FIG. 26 is illustrated in FIGS. 24 and 25. It can be seen from FIG. 24(*a*) in particular (a perspective view of the base) how base 800 has hub 820 and a single lumen 830 formed therein. Lumen 830 will have one or more walls, and FIG. 24(*a*) shows how these walls may have a feature, e.g. dent 832, which as explained below, is involved in forming a fluid path to the insertion portion received therein. FIG. 24(*b*) also shows how at least the top of the lumen may be shaped to mate with the top of the insertion portion housing, see for example, the shape of the top of housing 410 in FIG. 28.

Cross-section A-A from FIG. 24(*b*) then shows the profile of lumen 830 through the hub 820. In this exemplary embodiment, lumen 830 has a top section of greater width than a bottom section; a tapered cross-section. It can be seen from FIG. 28 how this shape corresponds to the shape of the cannula housing 410. Lumen 830 is not, however, limited to this shape and can be any shape or size that mates with the corresponding feature of the insertion portion. Cross-section A-A from FIG. 24(*b*) also shows the position of apertures 850 for coupling with a connector and dent or other feature 832.

Cross-section B-B from FIG. 24(*b*) shows the fit and position of hub 820 on base 800 in this exemplary embodiment, as well as the side profile of channel 860. As illustrated by FIGS. 24(*a*), (*b*) and (*c*), the hub 820 may include channels 860. These channels 860 may be of any shape or size. In various embodiments of the invention, these channels 860 are configured to form a fluid pathway with the at least two independent fluid sources (via the connector) and the insertion portion (not shown).

Figure 32:
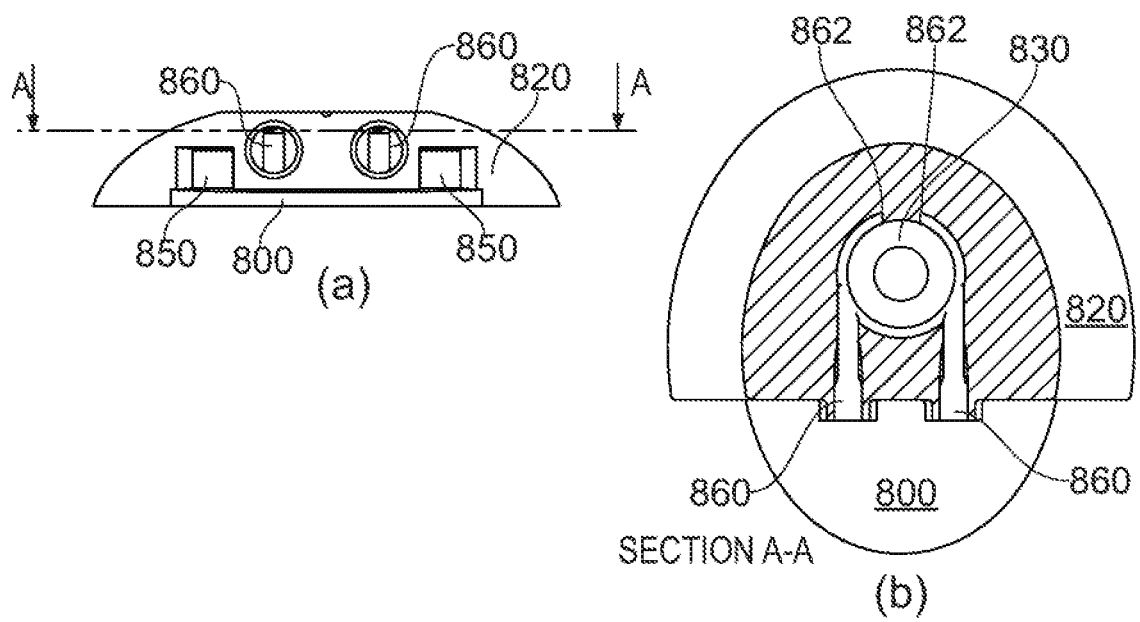
FIG. 32 includes views (a) and (b)

FIG. 25(*a*) shows, for example, how channels 860 may have a tapered cross-section in the direction of the lumen 830 and are separate from one another along their entire length. Channels 860 may of course have any cross-section that forms at least two separate fluid paths between the connector and the insertion portion. FIG. 32(*b*) (a cross-section of FIG. 32(*a*)) shows, for example, how the channels 860 may form a fluid path that extends towards and surrounds the exterior of housing of the insertion portion. As discussed in more detail below, the embodiment of FIG. 32 is for use with a cap element that has tracks on its inner surface for coupling with channels 860 so as to securely divide them into at least two independent fluid paths.

FIG. 28 shows how channels 860 may be used to couple with connector 200. In the illustrated embodiment, the connector 200 has self-penetrating cannulas as the fluid delivery conduits 216, 218, and these cannulas pierce or penetrate membranes or septems 880 located in an outlet or port of the channels 860 to form two independent fluid pathways for the fluids being administered. Such membranes or septums 880 may be made from any suitable material known in the art, e.g. silicone rubber or the like, and are typically formed as part of the neck of the channel 860.

FIG. 28 also shows an exemplary embodiment of insertion portion 400 comprised of a penetrating element 420 connected to and extending from a housing 410. The insertion portion is covered by a cap element or seal 700. In this exemplary embodiment, the cannula 420 is a multi-lumen cannula. It can be seen from FIG. 28 that lumen 830 includes at least one feature in a wall (e.g. an inner wall), e.g. dent 832, for coupling with a feature (e.g. a port or chamber entrance) of the insertion portion 400.

The insertion portion of each of the illustrated embodiments may be used for delivering fluid to a patient on a continuous and/or programmable basis over an extended period of time, for example, the administration of insulin or another active to a patient by means of a programmable external infusion device.

The insertion portion 400 from FIG. 28 and its positioning within base 800 and lumen 830 is shown further in FIG. 29. FIG. 29(a) is the underside of infusion set 1 in FIG. 26 showing in a similar manner to FIG. 25(a), how channels 860 have a tapered profile and extend towards lumen 830 and penetrating element 820. Each channel forms an independent fluid path from a connector to the penetrating element. FIG. 29(a) also shows how arms 220 of the connector are coupled with the base 800.

Figure 30:
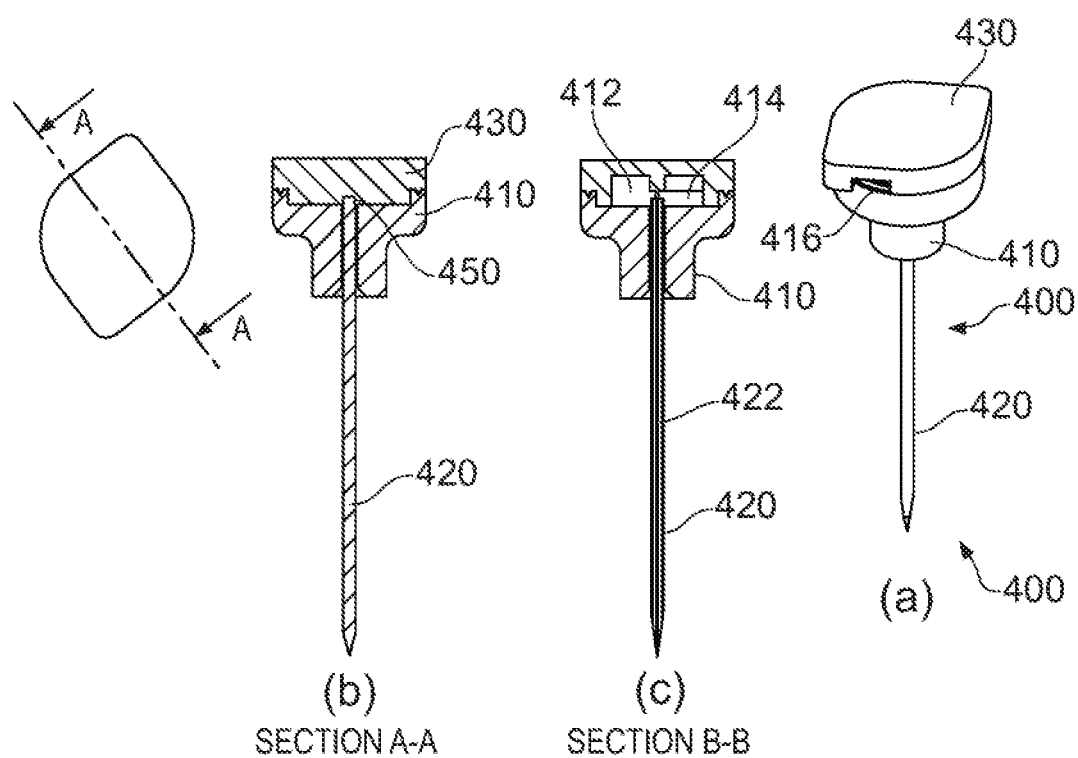
FIG. 30(a) is a perspective view of an insertion portion 400 according to the present invention.
FIG. 30(b) is cross-sectional view A-A and FIG. 30(c) is cross-sectional view B-B both showing the interior of the cannula housing and independent chambers 412, 414 for two independent fluid sources for the portion 400 of FIG. 30(a).
Figure 31:
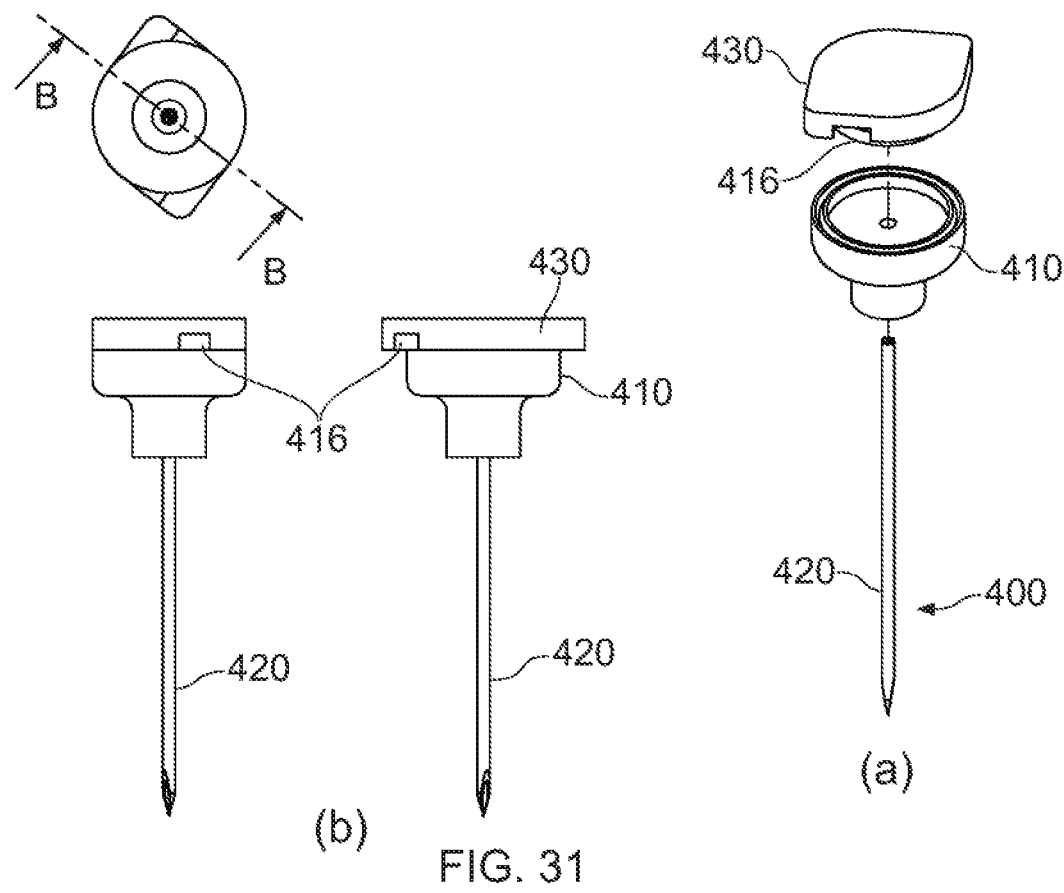
FIG. 31(a) is an exploded perspective view of the insertion portion 400 from FIG. 30(a).
FIG. 31(b) shows where cross-section B-B was taken for FIG. 30(c) and shows each independent chamber entrance 416.

FIG. 29(b) is the cross-section A-A shown in FIG. 29(a) which extends across channel 860. It can be seen from FIG. 29(b) how firstly connector 200 has penetrating elements 216, 218 which extend from the body into channels 860 to form a fluid path with a fluid delivery device (not shown). FIG. 29(b) also shows how insertion portion 400 has penetrating element 420 extending from a housing 410, the housing 410 having at least two interior chambers 412, 414, which are independent from each other in the sense that fluid contained in one chamber cannot come into contact with fluid contained in the other chamber. The chambers 412, 414 in the interior of housing 410 are illustrated more clearly in FIGS. 30 and 31. In this exemplary embodiment the housing has two chambers but the invention is not limited to this configuration; the housing may have two or more chambers, each chamber being in fluidic communication with an independent fluid source.

Finally, FIG. 29(b) shows how insertion portion 400 sits within lumen 830, and how a feature of one or more walls of the lumen, e.g. dent 832, can match or correspond with a feature of the insertion portion 400 to thereby form a fluid path. It will be understood by the skilled person that to deliver at least two independent fluids, there will be at least two independent fluid paths and hence at least two features of a lumen wall that match or correspond with at least two features of the insertion portion to form a fluid path.

In this exemplary embodiment, dent 832 in a wall (e.g. an inner wall) of the lumen 830 substantially aligns with a port or inlet for a chamber (here chamber 412) in the housing 410 of the insertion portion 400. The alignment of the dent 832 in the lumen wall and the port or inlet in the housing 410 of the insertion portion 400 forms a fluid pathway from the connector coupled to the base, to the insertion portion and ultimately to the patient via the infusion set placement site.

FIGS. 30(a) and 31(a) relate to the insertion portion 400 of FIGS. 27, 28 and 29 and show how this insertion portion 400 may be made up of a penetrating element (e.g. a cannula) 420 and housing 410, where housing includes top or cover 430. It can be seen from both FIGS. 30(a) and 31(a) how the housing 410 (here the top or cover 430 thereof) includes inlet or port 416 for coupling with a fluid path in the base.

Cross-sectional view A-A in FIG. 30(b) shows how the penetrating element 420 extends from housing 410 and how a top or cover 430 can seal the housing 410. Cross-sectional view B-B in FIG. 30(c) shows how the interior of housing 410 in this exemplary embodiment has one or more walls which define chambers 412, 414. The chambers 412, 414 are separated and spaced apart from each other, and in this embodiment the separation is achieved by an intermediary or dividing wall 418 in the housing. The chambers can be of any shape and size, and in various embodiments of the invention, the chambers occupy the majority (>50%) of the inner volume of the housing. It can be seen from FIG. 30(c) that in the illustrated embodiment, the cover 430 has wall 418 running along the length of its inner surface, such that chambers 412, 414 are formed when cover 430 is positioned to seal housing 410. The chambers 412, 414 may alternatively be formed completely within the interior of housing 410 and the cover 430 then positioned atop the inner chambers.

As illustrated by FIG. 31(b), the chambers 412, 414 may be located on opposite sides of the housing 410 and each have a separate port or inlet 416. Each port or inlet 416 may be located in the top 430 of the housing 410 or at any suitable position that provides fluidic communication with the fluid sources via the fluid delivery conduits of a connector as described herein. A fluid pathway is formed from the independent fluid delivery conduits via inlets 416 to chambers 412, 414 and penetrating element 420. Accordingly each chamber 412, 414 also has an outlet in fluidic communication with a lumen of the penetrating element 420. This can be seen from FIG. 30(c): the penetrating element 420 in the embodiment of FIG. 30(c) is a multi-lumen cannula having a piercing member 422 surrounded by two lumens, each lumen being independent from each other and running along the length of the cannula. The chambers 412, 414 may, however, have outlets in fluidic communication with a multi-lumen cannula which does not include a separate piercing member, e.g. a hard self-penetrating multi-lumen cannula. To avoid fluid mixing or contamination, each chamber 412, 414 is in fluidic communication with only one lumen of the cannula.

A multi-lumen cannula for use in the present invention (e.g. cannula 420 shown in FIG. 30(c)) includes two or more lumens, where each lumen may be adapted to deliver a particular fluid to an outlet of the cannula at the infusion placement site. The multiple lumens of the cannula are independent channels where each channel can be a single or multiple-lumen channel itself. The multiple lumens may be arranged in an array or as concentric lumens. In this way, a first discrete fluid pathway is created solely for the first fluid, and a second discrete fluid pathway is created solely for the second fluid. In various embodiments the first lumen (i.e. the lumen in fluidic communication with a first fluid) is an outer lumen and the second lumen is an inner lumen. In alternative embodiments the first lumen is an inner lumen and the second lumen is an outer lumen. In other embodiments, the lumens are arranged side-by-side along the length of the cannula such that the distal end of each lumen is separate from one another.

As illustrated in FIG. 30(b), the multi-lumen penetrating element 420 may have a notched end 450 at its proximal end. Such a notched end is advantageous because it prevents rotation of the penetrating element in the infusion set and thereby avoids mixing of the fluids contained and flowing between each chamber and the lumen of the penetrating element into the patient. A notched end can be introduced during manufacture of the infusion set and is therefore a straightforward and reliable mechanism for avoiding fluid contamination during use of the set.

As noted above, FIG. 32 includes cross-section A-A of channels 860 as FIG. 32(b). This cross-sectional view is an exemplary embodiment of a base 800 having a single lumen 830 and channels 860 which extend towards and substantially surround the lumen. In the illustrated embodiment, the lumen is circular but the invention is not limited to this shape; the lumen may for instance have a substantially rectangular, triangular or the like shape. Irrespective of the lumen shape, channels 860 may run around the edge (e.g. circumference) of the lumen so as to form a fluid pathway from the connector to the insertion portion. The channels 860 may run along the entire edge of the lumen, and are divided into at least two independent portions (not shown). In the illustrated embodiment of FIG. 32(b), the channels 860 each have a closed distal end 862. It follows from the discussion herein that channels 860 illustrated in FIG. 32(b) form two independent fluid pathways with an insertion portion (not shown), and may be used with a cover or cap (not shown) that has tracks on its inside surface and features in the one or more walls of the lumen which align with the chamber inlets of the housing. Such a cover or cap is shown in FIG. 37 and described below.

Figure 37:
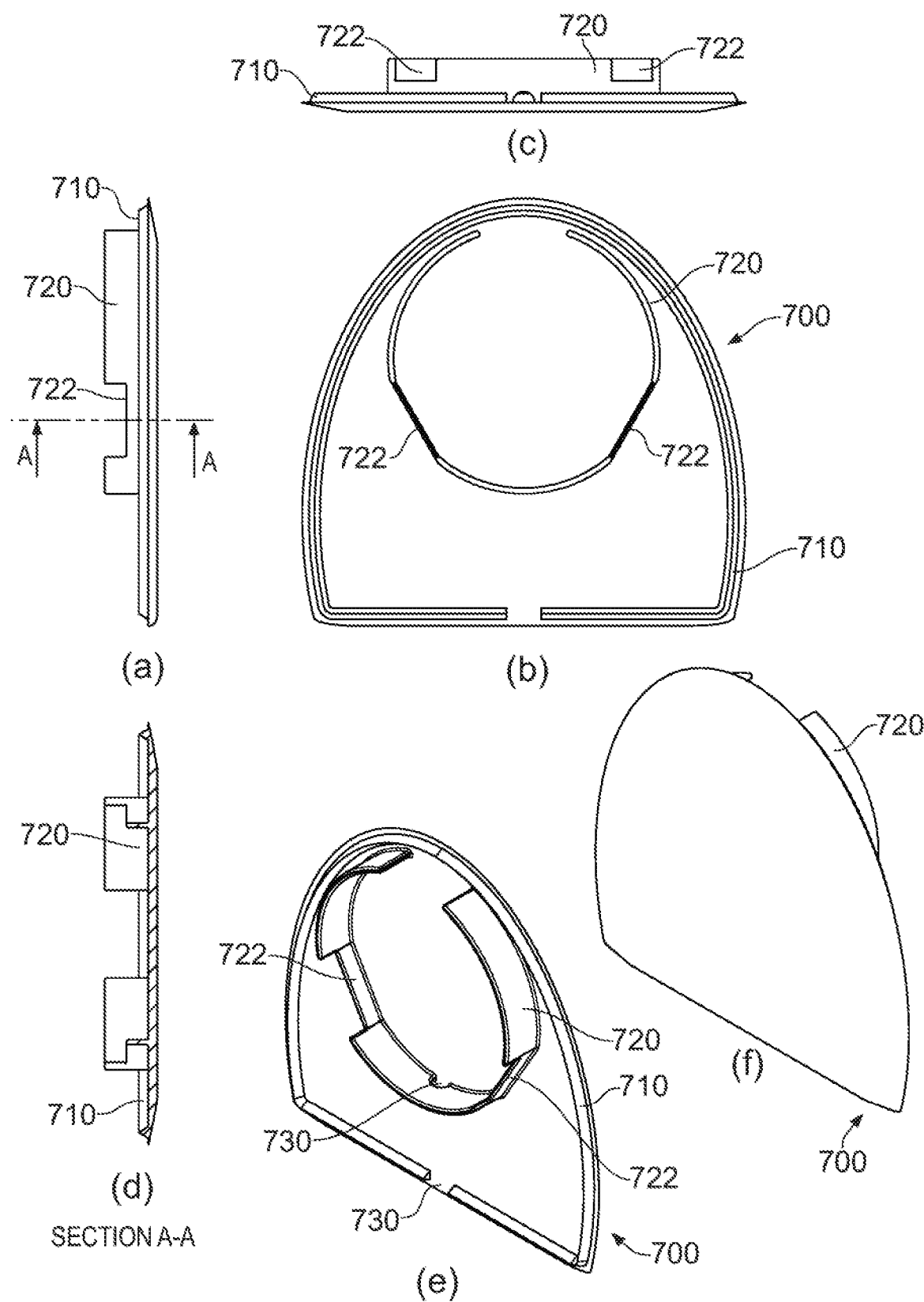
FIG. 37 includes views (a) to (f) of cap 700 showing the tracks on the inside or inner surface for coupling with the base 800. Also shown is groove 730 which forms part of the sensor portion of the infusion set.

FIG. 37 includes views (a) to (f) of cap element 700 that can be used to seal the infusion portion to the base and thereby form sealed fluid paths in channels 860 of FIG. 32(b). The cap element 700 can be coupled or secured to the base and/or insertion portion by any suitable mechanism. In the illustrated example, the cap includes multiple tracks formed on its underside that are adapted to mate with corresponding tracks on e.g. the hub of the base and/or the housing of the insertion portion. These tracks are not limited, and may take any suitable form to couple the cap 700 to the base and/or the insertion portion.

In various embodiments, the cap has at least one track 710 on its inside surface for coupling with the base. It can be seen from FIG. 37(b) and FIG. 37(e) how this track 710 may run along the edge of the inside surface, and may include at least one groove in its length. The invention is not, however, limited to this track configuration. The track 710 for coupling with the base may advantageously secure the cap 700 to the base in a non-removeable manner to improve patient safety and reduce mis-use of the infusion set. The track 710 may therefore be made from the same material as the rest of the cap, e.g. a plastic material such as polypropylene or the like.

In various embodiments, the cap 700 may further have at least one track 720 on its inside surface for coupling with channels in the base and the housing of the insertion portion. As discussed above, this track 720 may couple with one or more channels in the base and the housing of the insertion portion in order to form at least two independent sealed fluid paths from the connector to the insertion portion. The need to form sealed fluid paths means that the material of track 720 may differ from the material of track 710. In various embodiments of the invention, track 720 may be formed from a membrane material, such as silicone rubber or the like. Alternatively, the material of track 720 may be the same as the material of track 710. The track 720 may have at least two grooves 722 therein which are located in the track so as to align with the at least two entrances or inlets of the insertion portion and/or surface features in the walls of the lumen.

As shown in FIG. 37(e), both track 710 and track 720 may also have a groove 730 which forms part of the sensor portion disclosed in FIGS. 33, 34, 35 and 36. In various embodiments of the invention, the infusion set includes a sensor portion. Specifically, the sensor portion includes a sensor located within one of the lumen of the multi-lumen penetrating element, and a pathway extending from the infusion placement site to the fluid delivery device. This pathway may include a groove 340 in the housing of the insertion portion, see e.g. FIGS. 33 (a), (b), FIG. 34 and FIG. 35(b), a groove 870 in the base, see e.g. FIGS. 36(a) and 36(d), and one or more grooves 730 in cap 700 (see FIG. 37). Each of these grooves is substantially aligned in order for the sensor to monitor one or more body characteristic of a patient at the infusion placement site, and transmit this information to the fluid delivery device (e.g. infusion pump or the like).

Figure 33:
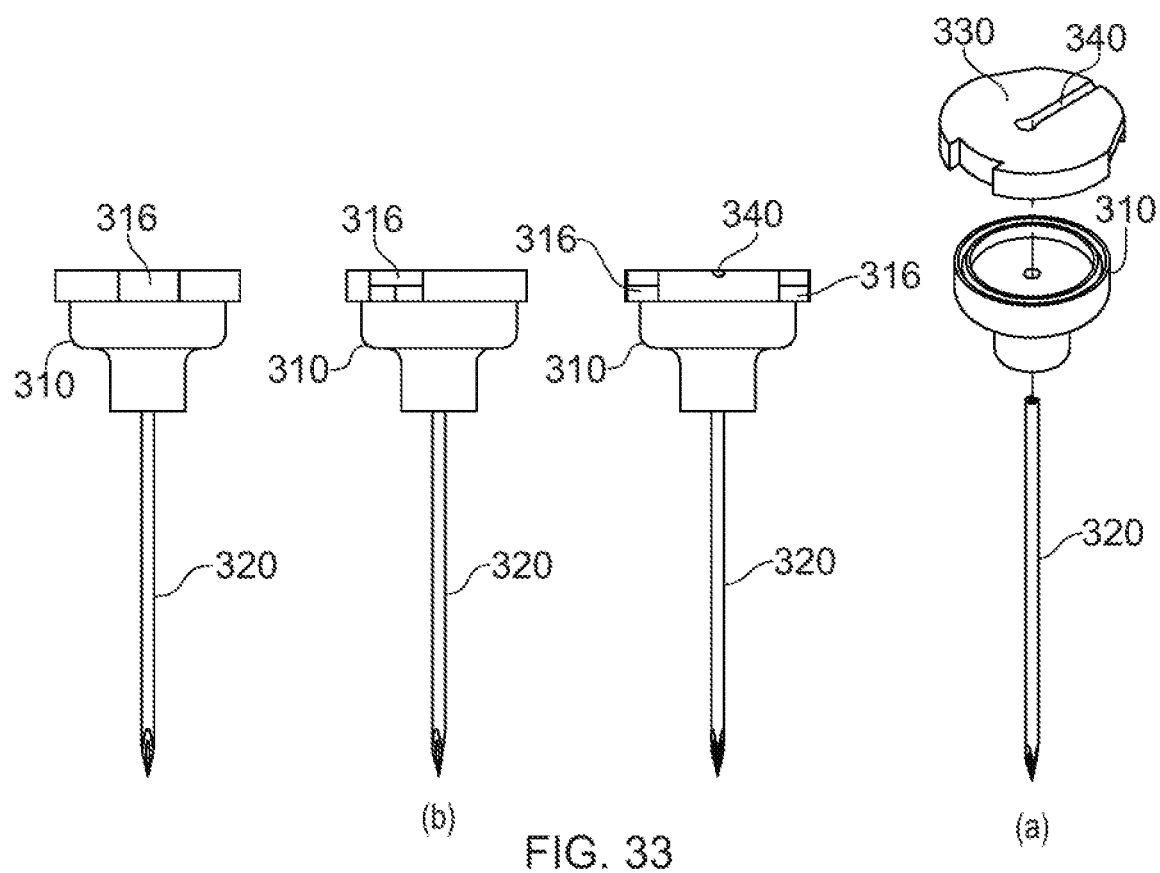
FIG. 33 includes views (a) and (b)
Figure 34A:
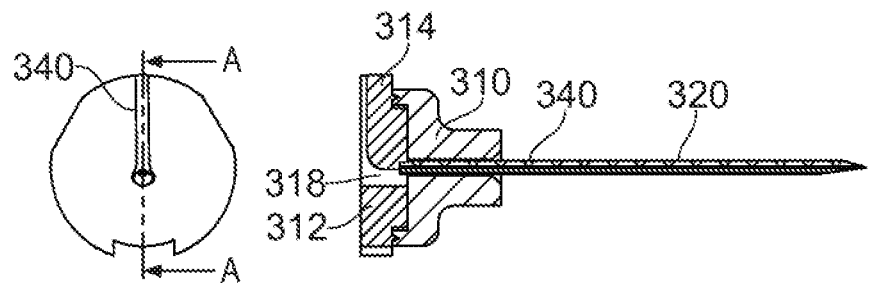
FIG. 34(a) is view A-A across groove 340 showing the sensor path through the housing 310 and along the tri-lumen cannula 320.
Figure 34B:
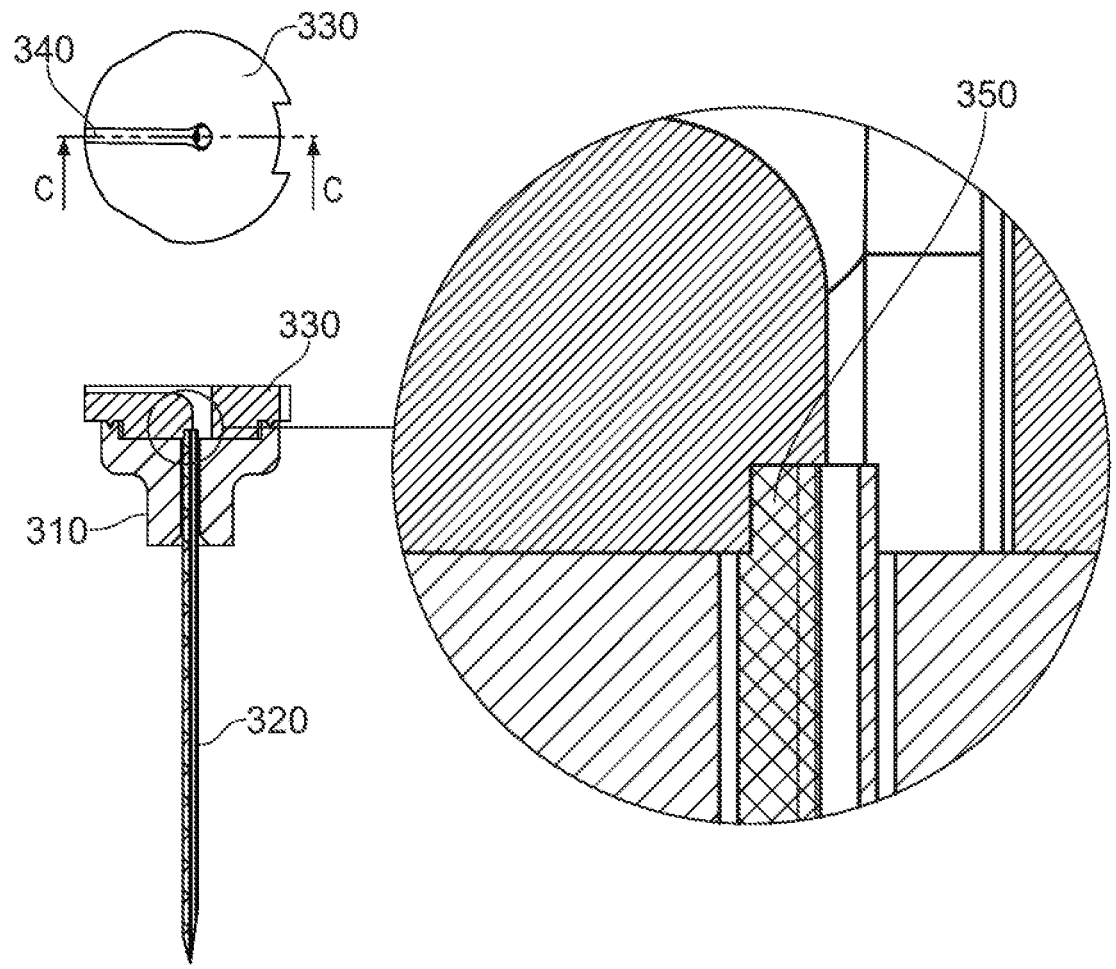
FIG. 34(b) is view C-C across groove 340 and an enlargement D showing a notch 350 at the proximal end of the cannula.
Figure 35:
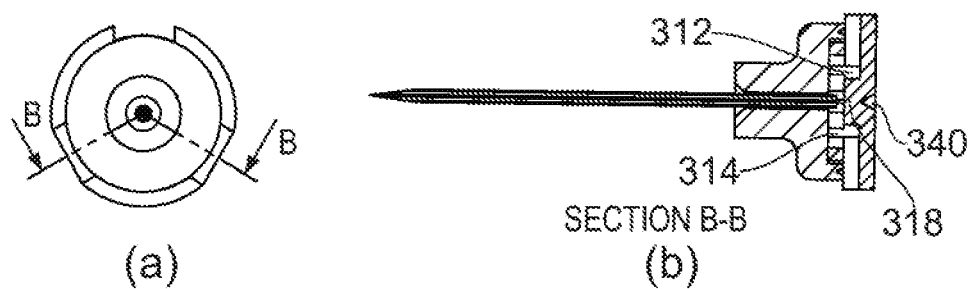
FIG. 35 is a cross-sectional view showing the first and second chambers 312, 314 and the tri-lumen cannula 320 along with groove 340 for the sensor.

An insertion portion for an infusion set comprising a sensor portion is shown in FIGS. 33, 34 and 35. In particular, FIG. 33 includes views (a) and (b) of a tri-lumen cannula 320 and housing 310 as the insertion portion 300. The tri-lumen cannula may correspond to the dual-lumen cannula described above, except that it further includes a groove 340 in the housing, e.g. in the top 330 of the housing, and an additional lumen for receiving the sensor. A dotted line on FIG. 33(a) shows how a sensor path may be formed from the groove 340 into the cannula 320.

The sensor path can also be seen in FIGS. 34 and 35. Features of these figures overlapping with the description of the dual-lumen cannula are shown with corresponding reference numerals, e.g. first and second chambers 312, 314 and dividing wall 318.

FIG. 33(b) shows the relative position of chamber entrances or inlets 316. The cross-sectional view B-B in FIG. 35 (b) shows chambers 312, 314 separated by intermediary wall 318. FIG. 34 includes views (a) and (b); FIG. 34(a) is a cross-section A-A across top 330 and sensor groove 340 showing chambers 312, 314 divided by 318 which has the sensor path running there-through into the multi-lumen cannula 320.

FIG. 34(b) is another cross-section C-C across top 330 and sensor groove 340. This figure also, however, includes detail, D, at a scale of 50:1, to show the notched end 350 of the cannula 320 which prevents rotation thereof between the separate chambers. This notched end may be included in any of the multi-lumen penetrating element(s) described herein.

A base for an infusion set comprising a sensor portion is shown in FIGS. 36(a) to (e). This base largely corresponds to the base shown in e.g. FIG. 26, except that the hub 820 further has a groove 870 formed therein for the sensor path. The groove 870 may extend from lumen 830 and be arranged to substantially align with a groove on an insertion portion received in the lumen 830 so as to form a sensor pathway towards the connector.

FIG. 36(d) is a perspective view of base 800 showing how groove 870 extends from lumen 830. It can also be seen from FIG. 36(d) how channels 860 are formed therein with distal end 862 and dent 832. Similar features can be seen in FIG. 36(a). FIG. 36(a) can also be compared with the underside of cover 700 and tracks 710, 720 in FIG. 37 to understand how the cover 700 engages with the base 800.

The sensor located within one of the lumen of the multi-lumen penetrating element can be any suitable sensor known in the art. During general operation, a biological sample (e.g. blood or other fluid), or a portion thereof, contacts the sensor (indirectly or directly) and allows measurement of one or more body characteristic. The sensor may therefore measure a concentration of an analyte of interest or a substance indicative of the concentration or presence of the analyte in fluid. In an exemplary embodiment of the invention, the sensor may be of the type that senses a product or reactant (e.g. $H_2O_2$) of an enzymatic reaction between an analyte (e.g. glucose) and an enzyme (e.g. glucose oxidase) in the presence of oxygen as a measure of the analyte in vivo or in vitro. Such sensors typically use an amperometric, coulometric, conductimetric, and/or potentiometric technique for measuring the analyte.

In various embodiments of the invention, the sensor portion of the infusion set monitors blood glucose levels and can be used in conjunction with automated and/or semi-automated medication infusion pumps. In additional embodiments, the sensor portion may be used to determine the levels of other agents, characteristics or compositions, such as hormones, cholesterol, medication concentrations, pH, oxygen saturation, viral loads (e.g. HIV) or the like.

Figure 36:
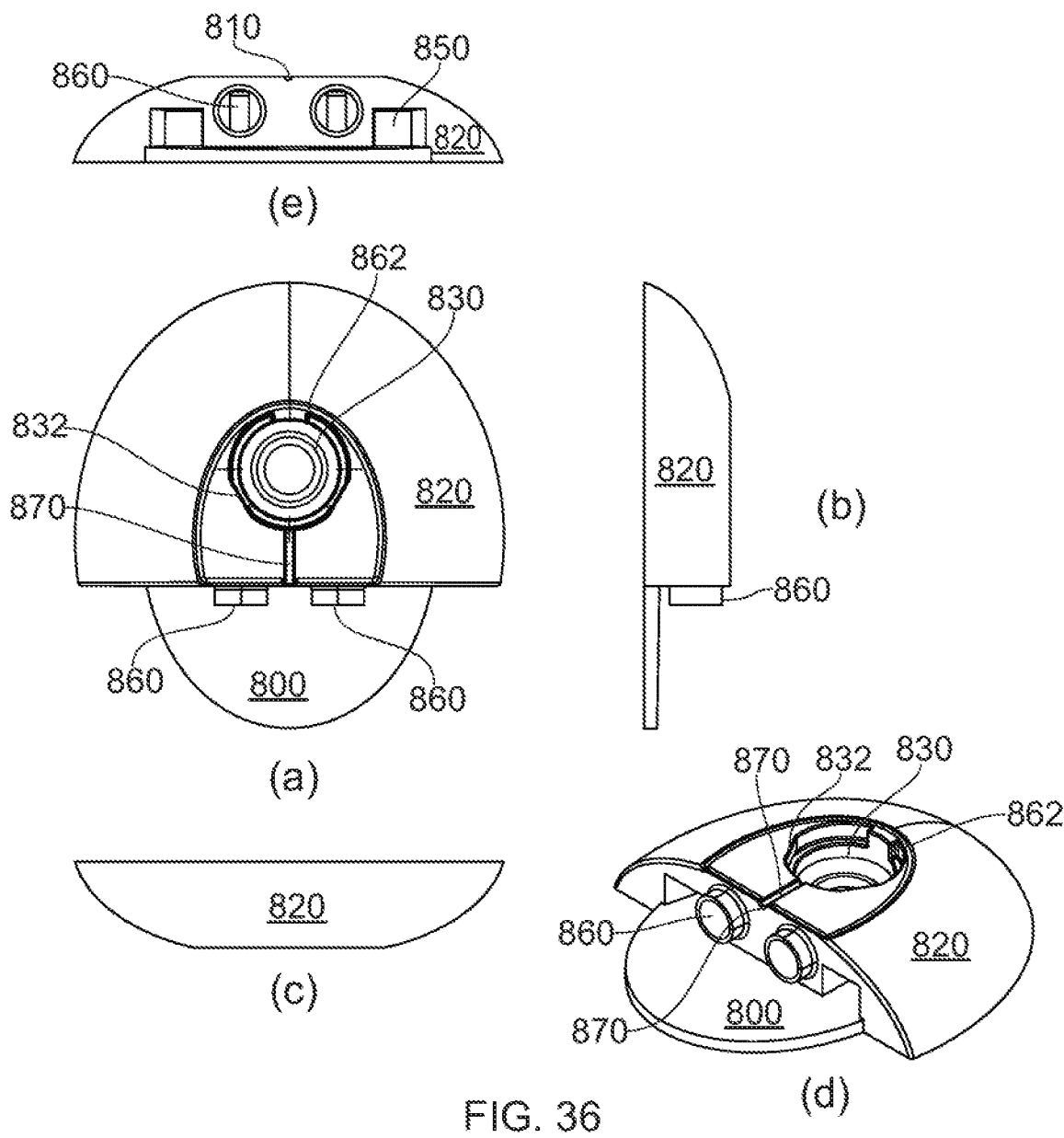
FIG. 36 is a representation of a base 800 for an infusion set 1 comprising a sensor portion.
Figure 38:
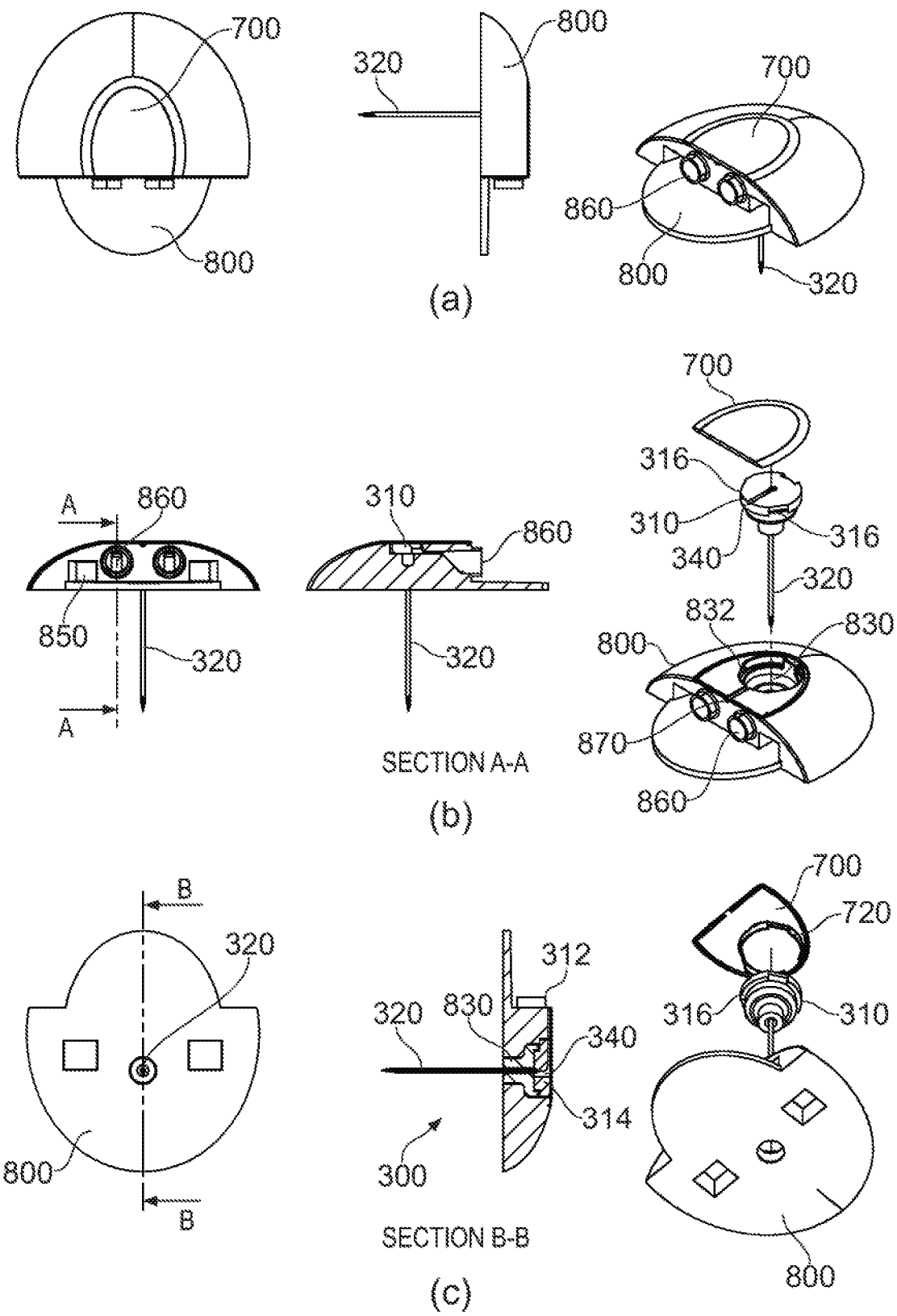
FIG. 38 includes views (a), (b) and (c)

FIG. 38 shows how the base 800 of FIG. 36, the cover 700 of FIG. 37 and the insertion portion 300 couple together. FIG. 38(a) is concerned with an assembled base 800, cover 700 and insertion portion. The penetrating element 320 of the insertion portion can be seen to extend from the underside of base 800 and cover 700 can be seen to seal the insertion portion within the base. FIG. 38(b) includes a cross-section A-A vertically across channel 860 to show the position of the insertion portion housing 310 relative to channel 860, and an exploded view of the various components. In the exploded view it can be seen how chamber entrances or inlets 316 formed in the insertion portion 300 align with dents 832 in the one or more walls of the lumen, and how groove 340 in the top of housing 310 aligns with groove 870 in the hub 820.

FIG. 38(c) includes a cross-section B-B across the underside of base 800 and penetrating element 320 to show the position of the insertion portion 300 in the lumen 830, and the position of the chambers 312, 314 either side of the sensor path 340. In the exploded view of FIG. 38(c), it can be seen how the cover 700 has tracks 720 on its underside which align with the openings or inlets 316 on the insertion portion housing 310.

The connector and infusion set of the present invention are suitable for infusing or delivering at least two independent fluids to a patient. The fluid contains an active, but the active is not limited and may include any drug, enzyme, antigen, hormone, vitamin or the like known in the art. In particular embodiments, the infusion set may be coupled to an external infusion device or pump. When coupled to an external infusion device, the infusion set may also include a disconnect cable or tube (e.g. as shown in FIG. 1) allowing the patient to easily disconnect the infusion set from the device or pump to go swimming, take a shower or the like, without having to entirely remove the infusion set from the body of the patient. Particular embodiments are directed towards use in humans, but in alternative embodiments, the infusion set may be used in animals.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the disclosure as defined by the claims or limitations on equivalents to the claims, and that other embodiments may be utilised and modifications may be made without departing from the scope of the claimed disclosure. Various embodiments of the present disclosure may suitably comprise, consist of, or consist essentially of, appropriate combinations of the disclosed elements, components, features, parts, steps, means etc. other than those specifically described herein. In addition, this disclosure may include other disclosures not presently claimed, but which may be claimed in future.

The invention claimed is:

1. A connector assembly for an infusion set comprising: a connector and a base, the connector comprising a body and at least one arm connected to the body which is configured to couple with the base of the infusion set, the base comprising an adhesive portion, a hub configured to couple with the connector, and a first lumen configured to receive a first insertion portion and a second lumen configured to receive a second insertion portion;
wherein the body has a first portion that corresponds with the first insertion portion and a second portion that corresponds with the second insertion portion, the first portion and the second portion are configured to be removably and replaceably coupled together;
wherein each of the first portion and second portion have a fluid delivery conduit, the conduits being configured to allow fluidic communication of the connector with at least two independent fluid sources;
wherein the first insertion portion is insertable into the first lumen of the base and the second insertion portion is insertable into the second lumen of the base at a substantially perpendicular orientation relative to an outer surface of a subject when the base is coupled to the outer surface of the subject.

2. The connector assembly according to claim 1, wherein the conduits are configured to allow fluidic communication of the connector with two to four, two to three, or two independent fluid sources.

3. The connector assembly according to claim 1, wherein the body comprises at least two penetrating elements.

4. The connector assembly according to claim 3, wherein each penetrating element of the at least two penetrating elements is associated with one of the fluid delivery conduits and each penetrating element extends from the body of the connector.

5. The connector assembly according to claim 1, wherein the at least one arm has a non-uniform cross-section and a coupler that comprises a hooked end or an inclined surface.

6. The connector assembly according to claim 1, wherein the first portion has one or more protrusion or rib extending outwardly from a surface, and the second portion has one or more complementary groove or recess formed within a surface, or wherein the second portion has one or more protrusion or rib extending outwardly from a surface, and the first portion has one or more complementary groove or recess formed within a surface.

7. The connector assembly according to claim 6, wherein the surface feature associated with the first portion is a rail type element and the surface feature associated with the second portion includes a channel that is sized and configured for receiving and reversibly coupling with the rail type element.

8. The connector assembly according to claim 6, wherein the first and second portions are connected with complementary male and female parts that form a bayonet connection.

9. An infusion set for administering multiple fluids to a subject, the infusion set comprising a base, an insertion portion, and a connector;

wherein the base comprises an adhesive portion, a hub configured to couple with the connector, and at least one lumen configured to receive the insertion portion;

wherein the insertion portion comprises at least one penetrating element comprising a multi-lumen cannula extending from a housing, the at least one penetrating element being coupled to and extending from the base to administer the multiple fluids sub- or trans-cutaneously to the subject when the housing is positioned in the at least one lumen;

wherein the connector comprises a body, at least one arm connected to the body which is configured to couple with the hub of the base, and at least two independent fluid delivery conduits which are configured to allow fluidic communication between at least two independent fluid sources and the at least one penetrating element;

wherein the base defines first and second dents within the at least one lumen that correspond with chamber entrances of the housing and are configured to fluidly couple the at least two independent fluid delivery conduits to separate lumens of the multi-lumen cannula.

10. The infusion set according to claim 9, wherein the housing has at least two chambers configured to allow fluidic communication between the at least two independent fluid sources and the at least one penetrating element, wherein the at least two chambers are independent from each other.

11. The infusion set according to claim 10, wherein the base has at least two channels which substantially align with the at least two chambers of the housing and are configured to allow fluidic communication with the at least two independent fluid sources.

12. The infusion set according to claim 10, wherein each of the at least two chambers of the housing has an opening for fluidic communication with the at least one penetrating element and an opening for fluidic communication with one of the fluid delivery conduits of the connector.

13. The infusion set according to claim 9, wherein the multi-lumen cannula has a first lumen with a distal end for fluid communication between the placement site and a first fluid source of the at least two independent fluid sources, and a second lumen with a distal end for fluid communication between the placement site and a second fluid source of the at least two independent fluid sources, wherein the first and second lumens are independent from each other.

14. The infusion set according to claim 9, further comprising a sensor portion, wherein the sensor portion has at least one sensor extending from the base which is configured for determining at least one body characteristic of the subject.

15. The infusion set according to claim 14, wherein the sensor portion comprises a lumen in the at least one penetrating element for the at least one sensor.

16. The infusion set according to claim 15, wherein the sensor portion further comprises a groove in the housing and a groove in the base.

17. The infusion set according to claim 9, further comprising a cap for coupling with said base, wherein the base has at least two channels configured to allow fluidic communication with the at least two independent fluid sources, and the cap has at least one track on its inside surface for coupling with said channels.

18. The infusion set according to claim 17, wherein the at least one track for coupling with the housing is formed from a membrane material.

* * * * *